US009388406B2

(12) United States Patent
Delisa et al.

(10) Patent No.: US 9,388,406 B2
(45) Date of Patent: Jul. 12, 2016

(54) SYSTEM USEFUL FOR REPORTING PROTEIN-PROTEIN INTERACTIONS IN THE BACTERIAL PERIPLASM

(75) Inventors: Matthew P. Delisa, Ithaca, NY (US); Thomas J. Mansell, Ithaca, NY (US)

(73) Assignee: Cornell University, Ithaca, NY (US)

( * ) Notice: Subject to any disclaimer, the term of this patent is extended or adjusted under 35 U.S.C. 154(b) by 116 days.

(21) Appl. No.: 13/129,527

(22) PCT Filed: Nov. 16, 2009

(86) PCT No.: PCT/US2009/064593
§ 371 (c)(1),
(2), (4) Date: Aug. 8, 2011

(87) PCT Pub. No.: WO2010/057097
PCT Pub. Date: May 20, 2010

(65) Prior Publication Data
US 2011/0287963 A1    Nov. 24, 2011

Related U.S. Application Data

(60) Provisional application No. 61/115,172, filed on Nov. 17, 2008.

(51) Int. Cl.
C40B 30/04    (2006.01)
C12Q 1/68     (2006.01)
C12N 15/10    (2006.01)

(52) U.S. Cl.
CPC ...... *C12N 15/1055* (2013.01); *C07K 2319/034* (2013.01); *C07K 2319/61* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 6,428,951 B1 | 8/2002 | Michnick et al. | |
| 2003/0165825 A1 | 9/2003 | Balint et al. | |
| 2003/0180937 A1 | 9/2003 | Georgiou et al. | |
| 2004/0038317 A1 | 2/2004 | Balint et al. | |

FOREIGN PATENT DOCUMENTS

| | | | |
|---|---|---|---|
| WO | 2007024877 A2 | 3/2007 | |
| WO | WO 2007/024877 A2 * | 3/2007 | ............ C40B 30/06 |

OTHER PUBLICATIONS

Nord et al in "Fluorescent detection of beta-lactamase activity in living *Escherichia coli* cells via esterase supplementation" (FEMS Microbiology Letters 2005, vol. 242, pp. 73-79, published online Nov. 10, 2004).*
GenBank Accession # AAB59737.1 downloaded Apr. 8, 2013.*

Hatzixanthis et al., "A Subset of Bacterial Inner Membrane Proteins Integrated by the Twin-Arginine Translocase," Molecular Microbiology 49(5):1377-1390 (2003).
Hennecke et al., "A ToxR-Based Two-Hybrid System for the Detection of Periplasmic and Cytoplasmic Protein-Protein Interactions in *Escherichia coli*: Minimal Requirements for Specific DNA Binding and Transcriptional Activation," Protein Engineering, Design & Selection 18(10):477-486 (2005).
Kolmar et al., "Membrane Insertion of the Bacterial Signal Transduction Protein ToxR and Requirements of Transcription Activation Studied by Modular Replacement of Different Protein Substructures," The EMBO Journal 14 (16):3895-3904 (1995).
Linderman et al., "Monitoring and Engineering Protein-Protein Interactions in the Bacterial Periplasm," Bioengineering Conference, IEEE 35th Annual Northeast (Apr. 3, 2009).

(Continued)

*Primary Examiner* — Catherine S Hibbert
(74) *Attorney, Agent, or Firm* — LeClairRyan, a Professional Corporation

(57) ABSTRACT

One aspect of the present invention relates to a reporter system for detection of protein-protein interactions in the periplasm of a prokaryotic host cell. The reporter system includes a first expression system which has a nucleic acid molecule encoding a first fragment of a reporter protein molecule, a nucleic acid molecule encoding a first signal sequence, and a nucleic acid molecule encoding a first member of a putative binding pair, where the nucleic acid molecule encoding the first fragment, the nucleic acid molecule encoding the first signal sequence, and the nucleic acid molecule encoding the first member of the putative binding pair are operatively coupled to permit their expression in a prokaryotic host cell as a first fusion protein. The reporter system also includes a second expression system which has a nucleic acid molecule encoding a second fragment of the reporter protein molecule, a nucleic acid molecule encoding a second signal sequence, and a nucleic acid molecule encoding a second member of the putative binding pair, where the nucleic acid molecule encoding the second fragment, the nucleic acid molecule encoding the second signal sequence, and the nucleic acid molecule encoding the second member of the putative binding pair are operatively coupled to permit their expression in a prokaryotic host cell as a second fusion protein, where, when expressed in a prokaryotic host cell, at least one of the first and the second fusion proteins are co-translationally transported to the periplasm where, when present, the first and second members of the putative binding pair bind together and the first and second fragments of the reporter protein molecule are reconstituted, thereby producing an active reporter protein. The reporter system may be used to carry out methods of identifying candidate compounds which bind to a target protein, identifying a candidate gene which modulates binding between a first protein and second protein, and identifying a candidate compound which modulates binding between a first protein and second protein.

56 Claims, 5 Drawing Sheets

(56) References Cited

OTHER PUBLICATIONS

Natale et al., "Sec- and Tat-Mediated Protein Secretion Across the Bacterial Cytoplasmic Membrane—Distinct Translocases and Mechanisms," Biochimica et Biophysica Acta 1778:1735-1756 (2008).
Steiner et al., "Signal Sequences Directing Cotranslational Translocation Expand the Range of Proteins Amenable to Phage Display," Nature Biotechnology 24(7):823-831 (2006).
Strauch and Georgiou, "A Bacterial Two-Hybrid System Based on the Twin-Arginine Transporter Pathway of E. coli," Protein Science 16:1001-1008 (2007).
Wehrman et al., "Protein-Protein Interactions Monitored in Mammalian Cells via Complementation of Beta-Lactamase Enzyme Fragments," PNAS 99(6):3469-3474 (2002).
Extended European Search Report for European Patent Application No. 09826911.1 (mailed May 29, 2012).
Nord et al. "Fluorescent Detection of Beta-Lactamase Activity in Living Escherichia coli Cells via Esterase Supplementation," FEMS Micro Ltrs 242:73-79 (2005).
GenBank Accession No. A39292.1 (Mar. 5, 1997).
GenBank Accession No. AAB59737.1 (Sep. 30, 2008).
ISA210 PCT International Search and Written Opinion for PCT/US2009/064593, filed Nov. 16, 2009.
European Examination Report for corresponding European Patent Application 09826911.1 (Nov. 20, 2013).
European Examination Report for corresponding European Patent Application 09826911.1 (Sep. 8, 2014).
Thie et al., "SRP and Sec Pathway Leader Peptides for Antibody Phage Display and Antibody Fragment Production in E. coli," New Biotechnology 25(1):49-54 (2008).

* cited by examiner

SYSTEM USEFUL FOR REPORTING PROTEIN-PROTEIN INTERACTIONS IN THE BACTERIAL PERIPLASM This application claims the benefit of U.S. Provisional Patent Application Ser. No. 61/115,172, filed Nov. 17, 2008.

This invention was made with government support under grant number 1R21CA132223 by the National Institutes of Health. The government has certain rights in this invention.

FIELD OF THE INVENTION

The present invention is directed to a system useful for reporting protein-protein interactions in the bacterial periplasm.

BACKGROUND OF THE INVENTION

Protein-protein interactions are key molecular events that integrate multiple gene products into functional complexes in virtually every cellular process. These cellular processes are mostly mediated by non-covalently interacting multi-protein complexes and can include, for example, transcription, translation, metabolic pathways or signal transduction pathways. Because such interactions mediate numerous disease states and biological mechanisms underlying the pathogenesis of bacterial and viral infections, identification of protein-protein interactions remains one of the most important challenges in the post-genomics era. The most widely used is the yeast two-hybrid assay (Y2H), which was developed in 1989 (Fields et al., "A Novel Genetic System to Detect Protein-protein Interactions," *Nature* 340; 245-246 (1989)). Briefly, this assay comprises two proteins fused to a split yeast transcription factor (originally GAL4) that binds a promoter upstream of a reporter protein. If the proteins interact, the activity of the transcription factor is reconstituted and transcription of the reporter protein is upregulated, providing a signal.

The yeast 2-hybrid (Y2H) system has been the tool of choice for revealing numerous protein-protein interactions that underly diverse protein networks and complex protein machinery inside living cells. Y2H assay has been used to generate protein interaction maps for humans (Rual J. F., et al., "Towards a Proteome-Scale Map of the Human Protein-protein Interaction Network," *Nature* 437:1173-1178 (2005)). Another important application of the Y2H methodology is the discovery of diagnostic and therapeutic proteins, whose mode of action is high-affinity binding to a target peptide or protein. For example, several groups have isolated antibody fragments that are readily expressed in the cytoplasm of cells where they bind specifically to a desired target (der Maur et al., "Direct in vivo Screening of Intrabody Libraries Constructed on a Highly Stable Single-chain Framework," *J Biol Chem* 277:45075-45085 (2002), Visintin M., et al., "Selection of Antibodies for Intracellular Function Using a Two-Hybrid in vivo System," *Proc Natl Acad Sci USA* 96:11723-11728 (1999)), and in certain instances ablate protein function (Tanaka T. et al., "Intrabodies Based on Intracellular Capture Frameworks that Bind the RAS Protein with High Affinity and Impair Oncogenic Transformation," *EMBO J.* 22:1025-1035 (2003), Tse E., et al., "Intracellular Antibody Capture Technology: Application to Selection of Intracellular Antibodies Recognising the BCR-ABL Oncogenic Protein," *J Mol Biol* 31 7:85-94 (2002)). The yeast two-hybrid assay is highly versatile and is still widely used for analysis of the complex interactions of eukaryotic cellular networks. However, it has several drawbacks, including in the fact that it requires the nuclear environment of the eukaryotic yeast host, which may differ from the interaction environment of the proteins of interest.

The Y2H system was initially developed by using yeast as a host organism. Numerous bacterial (B)2H systems are now common laboratory tools and represent an experimental alternative with certain advantages over the yeast-based systems (Hu J. C. et al., "*Escherichia coli* One- and Two-hybrid Systems for the Analysis and Identification of Protein-protein Interactions," *Methods* 20:80-94 (2000), Ladant D. et al., "Genetic Systems for Analyzing Protein-protein Interactions in Bacteria," *Res Microbiol* 151:711-720 (2000)). A number of these bacterial approaches employ split activator/repressor proteins; thus, they are functionally analogous to the GAL4-based yeast system (Dove S. L. et al., "Activation of Prokaryotic Transcription Through Arbitrary Protein-protein Contacts," *Nature* 386:627-630 (1997), Hu J. C., et al., "Sequence Requirements for Coiled-coils: Analysis with lambda Repressor-GCN4 Leucine Zipper Fusions," *Science* 250: 1400-1403 (1990), Joung J. K., et al., "A Bacterial Two-hybrid Selection System for Studying Protein-DNA and Protein-protein Interactions," *Proc Natl Acad Sci USA* 97:7382-7387 (2000)). Unfortunately, both Y2H and B2H GAL4-type assays are prone to a high frequency of false positives that arise from spurious transcriptional activation (Fields S., "High-throughput two-hybrid Analysis. The Promise and the Peril," *FEBS J* 272: 5391-5399 (2005)), and complicate the interpretation of interaction data. As proof, a comparative assessment revealed that >50% of the data generated using Y2H were likely to be false positives (von Mering C., et al., "Comparative Assessment of Large-scale Data Sets of Protein-protein Interactions," *Nature* 41 7:399-403 (2002)). To address this shortcoming, several groups have exploited oligomerization assisted reassembly of split enzymes such as adenylate cyclase (Karimova G., et al., "A Bacterial Two-hybrid System Based on a Reconstituted Signal Transduction Pathway," *Proc Natl Acad Sci USA* 95:5752-5756 (1998)), β-lactamase (Bla) (Wehrman T., et al., "Protein-protein Interactions Monitored in Mammalian Cells via Complementation of Beta-lactamase Enzyme Fragments," *Proc Natl Acad Sci USA* 99:3469-3474 (2002)), and dihydrofolate reductase (Pelletier J. N., et al., "An in vivo Library-versus-library Selection of Optimized Protein-protein Interactions," *Nat Biotech* 17:683-690 (1999), Pelletier J. N., et al., "Oligomerization Domain-directed Reassembly of Active Dihydrofolate Reductase from Rationally Designed Fragments," *Proc Natl Acad Sci USA* 95:12141-12146 (1998)), as well as split fluorescent proteins (Ghosh I. et al., "Antiparallel Leucine Zipper-Directed Protein Reassembly: Application to the Green Fluorescent Protein," *J Am Chem Soc* 122:5658-5659 (2000)). Alternatively, a number of methodologies for detecting interacting proteins in bacteria have been developed that do not rely on interaction-induced complementation of protein fragments, but instead use phage display (Palzkill T. et al., "Mapping Protein-ligand Interactions Using Whole Genome Phage Display Libraries," *Gene* 221:79-83 (1998)), FRET (You X., et al., "Intracellular Protein Interaction Mapping with FRET Hybrids," *Proc Natl Acad Sci USA* 103: 18458-18463 (2006)), and cytolocalization of GFP (Ding Z., et al., "A Novel Cytology-based, Two-hybrid Screen for Bacteria Applied to Protein-protein Interaction Studies of a Type IV Secretion System," *J Bacteriol* 184:5572-5582 (2002)).

In recent years, an alternative to the yeast two-hybrid assay has arisen in the form of the protein complementation assay (PCA). This method fuses the proteins of interest to a split reporter protein such as GFP (Cabantous, S. et al., "Recent Advances in GFP Folding Reporter and Split-GFP Solubility Reporter Technologies. Application to Improving the Folding and Solubility of Recalcitrant Proteins from *Mycobacterium Tuberculosis*," *J Struct Funct Genomics* 6:113-119 (2005), Cabantous, S. et al., "In vivo and in vitro Protein Solubility Assays Using Split GFP," *Nat Methods* 3:845-54 (2006)), YFP (Bracha-Drori, K. et al., "Detection of Protein-protein Interactions in Plants Using Bimolecular Fluorescence Complementation," *Plant J* 40:419-427 (2004)), luciferase (Kim, S. B. et al., "High-throughput Sensing and Noninvasive Imaging of Protein Nuclear Transport by Using Reconstitution of Split *Renilla* Luciferase," *Proc Natl Acad Sci USA* 101:11542-11547 (2004)), dihydrofolate reductase (Remy, I. et al., "Detection of Protein-protein Interactions Using a Simple Survival Protein-fragment Complementation Assay Based on the Enzyme Dihydrofolate Reductase," *Nat Proto* 2:2120-2125 (2007)), or β-lactamase (Galarneau, A. et al., "Beta-lactamase Protein Fragment Complementation Assays as in vivo and in vitro Sensors of Protein-protein Interactions," *Nat Biotechnol* 20:619-22 (2002), Wehrman, T. et al., "Protein-protein Interactions Monitored in Mammalian Cells via Complementation of Beta-lactamase Enzyme Fragments," *Proc Natl Acad Sci USA* 99:3469-3474 (2002)). Using protein engineering techniques, split proteins whose individual fragments are inactive can be developed. Upon interaction of the proteins of interest, the split reporter protein regains its activity. Versions of a split β-lactamase (Bla) protein complementation assay for monitoring protein-protein interactions in mammalian cells have been developed (Galarneau, A. et al., "Beta-lactamase Protein Fragment Complementation Assays as in vivo and in vitro Sensors of Protein-protein Interactions," *Nat Biotechnol* 20:619-22 (2002), Wehrman, T. et al., "Protein-protein Interactions Monitored in Mammalian Cells via Complementation of Beta-lactamase Enzyme Fragments," *Proc Natl Acad Sci USA* 99:3469-3474 (2002)). These versions however contain no signal sequence for protein transport, and thus the proteins were expressed in the cytoplasm of *E. coli*. Following expression, the Bla (β-lactamase) activity was measured in vitro by nitrocefin colorimetric assay. One limitation of cytoplasmic expression is that cytoplasmic β-lactamase (Bla) is incapable of conferring resistance to ampicillin and thus genetic selection is not possible. In one version, Wehrman et al. employed prototypical Sec signal peptides for delivery of the fragments into the periplasm by the post-translational Sec export pathway (Wehrman, T. et al., "Protein-protein Interactions Monitored in Mammalian Cells via Complementation of Beta-lactamase Enzyme Fragments," *Proc Natl Acad Sci USA* 99:3469-3474 (2002)). Following export, both fragments localize to the periplasm and cells can be selected on ampicillin. The limitation of this approach is that it uses post-translational Sec export signals. The proteins under investigation may fold fully inside the cytoplasm thereby limiting their potential translocation across the cytoplasmic membrane. They may also interact in the cytoplasm prior to export and thus not be exported to the periplasm. A further limitation of this approach is the fact that only one pair of small peptides was tested for interaction; whether split Bla (β-Lactamase) could be used to report the interactions between globular proteins was not demonstrated. Thus, to date there have been no reports detailing the use of split protein fragments for monitoring protein-protein interactions in the bacterial periplasm.

The present invention is directed to overcoming these and other deficiencies in the art.

SUMMARY OF THE INVENTION

In one aspect, the present invention relates to a reporter system for detection of protein-protein interactions in the periplasm of a prokaryotic host cell. The reporter system includes a first expression system which has a nucleic acid molecule encoding a first fragment of a reporter protein molecule, a nucleic acid molecule encoding a first signal sequence, and a nucleic acid molecule encoding a first member of a putative binding pair, where the nucleic acid molecule encoding the first fragment, the nucleic acid molecule encoding the first signal sequence, and the nucleic acid molecule encoding the first member of the putative binding pair are operatively coupled to permit their expression in a prokaryotic host cell as a first fusion protein. The reporter system also includes a second expression system which has a nucleic acid molecule encoding a second fragment of the reporter protein molecule, a nucleic acid molecule encoding a second signal sequence, and a nucleic acid molecule encoding a second member of the putative binding pair, where the nucleic acid molecule encoding the second fragment, the nucleic acid molecule encoding the second signal sequence, and the nucleic acid molecule encoding the second member of the putative binding pair are operatively coupled to permit their expression in a prokaryotic host cell as a second fusion protein. When expressed in a prokaryotic host cell, at least one of the first and the second fusion proteins are co-translationally transported to the periplasm where, when present, the first and second members of the putative binding pair bind together and the first and second fragments of the reporter protein molecule are reconstituted, thereby producing an active reporter protein.

Another aspect of the present invention relates to a method of identifying a candidate protein which binds a target protein. This method includes providing a first expression system comprising a nucleic acid molecule encoding a first fragment of a reporter protein molecule, a nucleic acid molecule encoding first signal sequence, and a nucleic acid molecule encoding a target protein, where the nucleic acid molecule encoding the first fragment, the nucleic acid molecule encoding the first signal sequence, and the nucleic acid molecule encoding the target protein are operatively coupled to permit their expression in a prokaryotic host cell as a first fusion protein. This method also includes providing a second expression system comprising a nucleic acid molecule encoding a second fragment of the reporter protein molecule, a nucleic acid molecule encoding a second signal sequence, and a nucleic acid molecule encoding a candidate protein, where the nucleic acid molecule encoding the second fragment, the nucleic acid molecule encoding the second signal sequence, and the nucleic acid molecule encoding the candidate protein are operatively coupled to permit their expression in a prokaryotic host cell as a second fusion protein. This method further includes transforming a prokaryotic host cell with the first expression system and the second expression system and culturing the transformed prokaryotic host cell under conditions effective to express the first and the second fusion proteins and to transport the first fusion protein and the second fusion protein to the prokaryotic host cell's periplasm, with at least one of the first fusion protein or the second fusion protein being co-translationally transported to the periplasm. The prokaryotic host cells with reporter protein molecule activity are detected as those where binding between the candidate protein and the target protein has occurred. The candidate protein is identified as having the ability to bind to the target protein based on whether the host cell has reporter protein activity.

Another aspect of the present invention is related to a method of identifying a candidate gene which modulates the binding between a first protein and a second protein. This method includes providing a first expression system comprising a nucleic acid molecule encoding first fragment of a reporter protein molecule, a nucleic acid molecule encoding a first signal sequence, and a nucleic acid molecule encoding a first protein, where the nucleic acid molecule encoding the first fragment, the nucleic acid molecule encoding the first signal sequence, and the nucleic acid molecule encoding the first protein are operatively coupled to permit their expression in a prokaryotic host cell as a first fusion protein. This method also includes providing a second expression system for expressing the second protein comprising a nucleic acid molecule encoding a second fragment of the reporter protein molecule, a nucleic acid molecule encoding a second signal sequence, and a nucleic acid molecule encoding a second protein, where the nucleic acid molecule encoding the second fragment, the nucleic acid molecule encoding the second signal sequence, and the nucleic acid molecule encoding the second protein are operatively coupled to permit their expression in a prokaryotic host cell as a second fusion protein. This method further involves providing a candidate gene in a form suitable for expression in a prokaryotic host cell, transforming the prokaryotic host cell with the first expression system, the second expression system, and the candidate gene, and culturing the transformed prokaryotic host cell under conditions effective to, in the absence of the candidate gene, express the first fusion protein, the second fusion protein, and the protein encoded by the candidate gene and transport the first fusion protein and the second fusion protein to the prokaryotic host cell's periplasm with at least one of the first fusion protein or the second fusion protein being co-translationally transported to the periplasm. Any reporter activity in the transformed prokaryotic host cell is detected, and prokaryotic host cells, with reporter activity that is different than that achieved without transformation of the candidate gene are identified, as containing a candidate gene which modulates binding between the first and second proteins.

Another aspect of the present invention is related to a method of identifying a candidate compound which modulates binding between a first protein and a second protein. This method includes providing a first expression system comprising a nucleic acid molecule encoding first fragment of a reporter protein molecule, a nucleic acid molecule encoding a first signal sequence, and a nucleic acid molecule encoding a first protein, where the nucleic acid molecule encoding the first fragment, the nucleic acid molecule encoding the first signal sequence, and the nucleic acid molecule encoding the first protein are operatively coupled to permit their expression in a prokaryotic host cell as a first fusion protein. This method also includes providing a second expression system for expressing the second protein comprising a nucleic acid molecule encoding a second fragment of the reporter protein molecule, a nucleic acid molecule encoding a second signal sequence, and a nucleic acid molecule encoding a second protein, where the nucleic acid encoding the second fragment, the nucleic acid encoding the second signal sequence, and the nucleic acid encoding the second protein are operatively coupled to permit their expression in a prokaryotic host cell as a second fusion protein. This method further involves providing a candidate compound, transforming a host prokaryotic cell with the first expression system and the second expression system, and culturing the transformed host prokaryotic cell under conditions effective to express the first and the second fusion proteins and transport the first fusion protein and the second fusion protein to the prokaryotic host cell's periplasm with at least one of the first fusion protein or the second fusion protein being co-translationally transported to the periplasm. The candidate compound is contacted with the cultured prokaryotic host cell. The reporter activity is detected in the transformed prokaryotic host cell, and candidate compounds contacting the prokaryotic host cells, with reporter activity that is different than that achieved in transformed prokaryotic host cells not contacted with the candidate compound are identified as modulating binding between the first protein and the second protein.

While numerous assays exist for detecting protein interactions in the cytoplasm of living cells, the major advantage of the present invention is that it can be used to assay for protein-protein interactions in the periplasmic compartment of bacteria. Such an assay would be significant because of the importance of the bacterial periplasm in a large number of biotechnological applications. This importance stems from several unique features of the periplasm relative to other sub-cellular compartments. For instance, proteins that require disulfide bonds for correct folding can only adopt a native conformation when localized in the oxidizing environment of the bacterial periplasm (disulfide bonds do not normally form in the cytoplasm of bacteria). Examples of disulfide-bond containing proteins of biotechnological relevance include proteins and protein fragments of the immunoglobulin family (e.g., IgGs). The ability to detect protein interactions in the periplasm can easily be combined with the ability to express full-length IgGs or fragments derived thereof (e.g., single-chain Fv (scFv)) in the periplasm and opens the door to a cell-based selection system for isolating and engineering virtually all types of antibodies or other immune/non-immune binding proteins. Since the technology described above only requires the antigen or domains of the antigen to be expressed in the periplasm, this technology should enable the selection of antibodies against both soluble and membrane proteins. Since many complex membrane proteins can be expressed in the inner membrane of E. coli (e.g., GPCRs, ion channels, efflux pumps, etc.), this technology should enable isolation of antibodies or other binding proteins that interact with exposed loops of membrane proteins. Such a feat is difficult or impossible using traditional antibody selection methods (e.g., cell surface display, phage display). More recently, the development of N-linked glycosylation in bacteria opens the bacterial periplasm as a compartment for attaching N-glycans to specific residues in recombinant proteins. Another advantage of the periplasm is that isolation of recombinant proteins from this compartment is greatly simplified compared to isolation from the more crowded cytoplasm. To accomplish this while also overcoming previous limitations of split β-lactamase systems in E. coli, a preferred embodiment of the present invention is co-expression of β-lactamase fragment fusions that are engineered with co-translational export signals (e.g., signal peptides from the E. coli DsbA protein). The advantage of such export signals is that at least one or both fragments of the reporter protein, and the interacting proteins (members of the putative binding pair) to which they are fused, are localized directly into the periplasm with little or no residence time in the cytoplasm. As a result, premature interaction between the proteins under investigation is effectively eliminated.

BRIEF DESCRIPTION OF THE DRAWINGS

FIG. 2A shows a schematic drawing of the two-plasmid system comprising genes of interest fused to α and ω β-lactamase fragments. Fos and Jun are used here as examples, and putative binding partners of interest would replace Fos and Jun in their respective constructs. FIG. 2B shows spot plating of Fos and Jun leucine zippers on 50 µg/ml Amp. GCN4, another leucine zipper, but one that does not interact with Fos, is used as a negative control. FIG. 2C shows spot plating as in FIG. 2B of antibody fragment scFv-GCN4 and its antigen, the GCN4 leucine zipper. GCN4-PP is a double point mutant to wild-type GCN4 that reduces homodimerization of the leucine zippers. Jun is used as a negative control. FIG. 2D shows spot plating of scFv D10, with affinity to phage protein Gpd. Jun and GCN4 used as negative controls.

FIG. 3A shows spot plating as in FIG. 2B of Fos/Jun variants. Notations such as L3V refer replacement of leucine 3 with valine, not necessarily residue 3. Similar growth for all variants was confirmed on Cm/Kan plates. FIG. 3B shows MIC (blue) and MBC (red) measurements of Fos and Jun variants as shown in FIG. 3A.

DETAILED DESCRIPTION OF THE INVENTION

Figure 1:
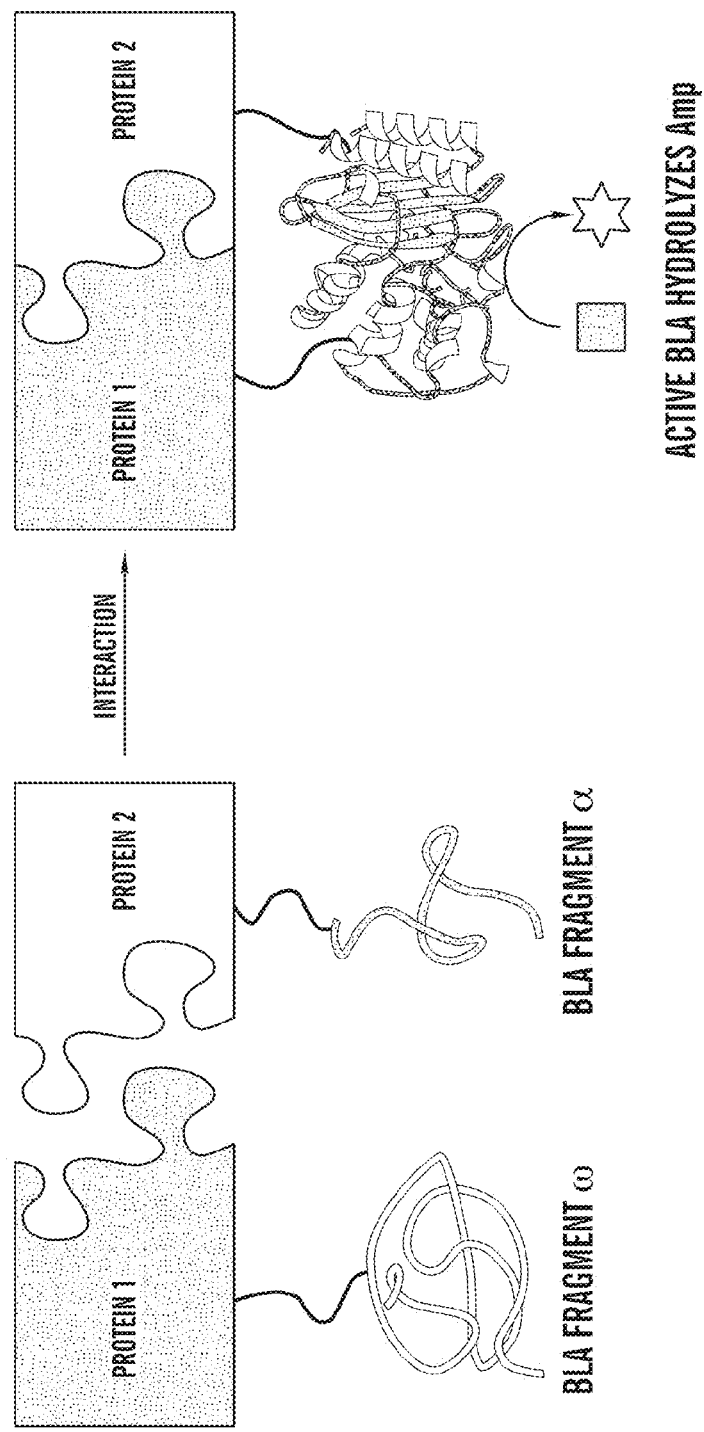
FIG. 1 is a schematic drawing showing protein 1 to protein 2 interactions complementing the two split fragments of β-lactamase. This arrangement enables the enzyme to hydrolyze ampicillin and cells to grow in the presence of the antibiotic.

One aspect of the present invention relates to a reporter system (also described herein as protein complementation system) which can be used to detect, protein-protein interactions. FIG. 1 shows one embodiment of the present invention. FIG. 1 shows protein 1 and protein 2 attached to two fragments of Bla. The proteins interact with one another and lead to complementation of the Bla fragments thus reconstituting the reporter activity. Bacterial cells transformed with this system will survive on ampicillin media. The reconstituted reporter activity of Bla leads to hydrolysis of ampicillin and enables the bacterial cells to survive on ampicillin media.

In one aspect, the present invention relates to a reporter system for detection of protein-protein interactions in the periplasm of a prokaryotic host cell. The reporter system includes a first expression system which has a nucleic acid molecule encoding a first fragment of a reporter protein molecule, a nucleic acid molecule encoding a first signal sequence, and a nucleic acid molecule encoding a first member of a putative binding pair, where the nucleic acid molecule encoding the first fragment, the nucleic acid molecule encoding the first signal sequence, and the nucleic acid molecule encoding the first member of the putative binding pair are operatively coupled to permit their expression in a prokaryotic host cell as a first fusion protein. The reporter system also includes a second expression system which has a nucleic acid molecule encoding a second fragment of the reporter protein molecule, a nucleic acid molecule encoding a second signal sequence, and a nucleic acid molecule encoding a second member of the putative binding pair, where the nucleic acid molecule encoding the second fragment, the nucleic acid molecule encoding the second signal sequence, and the nucleic acid molecule encoding the second member of the putative binding pair are operatively coupled to permit their expression in a prokaryotic host cell as a second fusion protein. When expressed in a prokaryotic host cell, at least one of the first and the second fusion proteins are co-translationally transported to the periplasm where, when present, the first and second members of the putative binding pair bind together and the first and second fragments of the reporter protein molecule are reconstituted, thereby producing an active reporter protein.

The reporter system of the present invention is useful in detecting interaction between, for example, a known first member of a putative binding pair and a second member, which was previously not known to bind the first member. The method detects the interaction of the first member with the second member by bringing into close proximity members of a fragment pair of a reporter protein, such that the reporter protein is reassembled to its original functionality or enzymatic activity. The fragments of the reporter protein of the present invention can interact to produce a detectable signal such as a visible phenotypic change or antibiotic resistance. This system should enable, for example, the identification of molecules and/or genes that promote or inhibit key protein interactions, existing in a range of cell types, phyla and species, via high-throughput screens.

As used herein, a "reporter protein" refers to a protein which can be separated into two or more individual protein fragments, where the reporter protein fragments are capable of associating with each other to generate a detectable signal, or are capable of associating with each other and one or more additional substances to generate a detectable signal, and which do not individually generate the detectable signal. The functional fragments of a reporter protein of interest can be identified by methods well known in the art. For example, it can involve preparing a multiplicity of fragment pair members with breaks within a solvent exposed loop or a flexible loop defined by tertiary or secondary structure analysis to obtain a fragment pair library. The fragment pair members can be, for example, expressed in a multiplicity of host cells, and the host cells exhibiting a directly detectable signal associated with the reporter protein of interest can be isolated as indicative of containing fragment pair members that functionally reconstitute the reporter protein. Plasmids containing expression systems coding for the fragment pair members can then be sequenced to identify functional fragment pairs of the reporter protein. Other methods of breaking proteins into fragments are known in the art and can be applied to the present invention as long as the reporter protein functions in a manner described supra.

In a preferred embodiment the reporter system comprises the antibiotic resistance enzyme, β-lactamase as a reporter protein molecule. However, fragment pairs of other enzymes that provide for antibiotic resistance are also included in the present invention, including, for example, aminoglycoside phosphotransferases, particularly neomycin phosphotransferase, chloramphenicol acetyl transferase, and tetracycline resistance protein (Backman et al., "Tetracycline Resistance Determined by pBR322 is Mediated by One Polypeptide," *Gene* 26:197 (1983), which is hereby incorporated by reference in its entirety). Other proteins that can directly elicit a visible phenotypic change such as a color change or fluorescence emission also are applicable to the present invention. Examples of such proteins include β-galactosidase and green fluorescent protein (GFP) or other related fluorescent proteins.

The reporter protein molecule can be selected from a group consisting of a monomeric protein, a multimeric protein, a monomeric receptor, a multimeric receptor, a multimeric biomolecular complex, adenylate cyclase, alkaline phosphatase, β-lactamase, cellulase, chloramphenicol acetyl transferase (CAT), disulfide bond oxidase A (DsbA), maltose binding protein (MBP), methyltransferase, dihydrofolate reductase (DHFR), luciferase, thymidylate synthase, thymidine kinase, Trp1 N-(5'-phosphoribosyl)-anthranilate isomerase, ubiquitin, and all fluorescent proteins including green fluorescent protein (GFP), blue fluorescent protein (BFP), cyan fluorescent protein (CFP), red fluorescent protein (RFP), yellow fluorescent protein (YFP), monomeric RFP (mRFP), mCherry, mOrange, mBanana, mStrawberry, mHoneydew, tdTomato, and mTangerine.

The β-lactamase of *E. coli* is a 286 amino acid (including the signal sequence) product of the ampicillin resistance gene of plasmid pBR322 (Sutcliffe J G., "Nucleotide Sequence of the Ampicillin Resistance Gene of *Escherichia coli* Plasmid pBR322," *Proc Natl Acad Sci USA* 75(8): 3737-41 (1978), which is hereby incorporated by reference in its entirety) and has the following amino acid sequence (Genbank ID AAB59737.1) (SEQ ID NO: 1):

```
  1 msiqhfrval ipffaafclp vfahpetlvk vkdaedqlga rvgyieldln 51 sgkilesfrp eerfpmmstf kvllcgavls rvdagqeqlg rrihysqndl 101 veyspvtekh ltdgmtvrel csaaitmsdn taanllltti ggpkeltafl 151 hnmgdhvtrl drwepelnea ipnderdttm paamattlrk lltgelltla 201 srqqlidwme adkvagpllr salpagwfia dksgagergs rgiiaalgpd 251 gkpsrivviy ttgsqatmde rnrqiaeiga slikhw
```

The β-lactamase reporter protein molecule may be split into a first fragment and a second fragment. The first fragment of the β-lactamase reporter protein can comprise an α fragment with residues 1-196 of the β-lactamase, where the α fragment has the following amino acid sequence (SEQ ID NO: 2):

```
  1 msiqhfrval ipffaafclp vfahpetlvk vkdaedqlga rvgyieldln 51 sgkilesfrp eerfpmmstf kvllcgavls rvdagqeqlg rrihysqndl 101 veyspvtekh ltdgmtvrel csaaitmsdn taanllltti ggpkeltafl 151 hnmgdhvtrl drwepelnea ipnderdttm paamattlrk lltgel
```

The second fragment of the β-lactamase reporter protein comprises ω fragment with residues 197-286 of the β-lactamase, where the ω fragment has the following amino acid sequence (SEQ ID NO: 3):

```
  1 ltlasrqqli dwmeadkvag pllrsalpag wfiadksgag ergsrgiiaa 51 lgpdgkpsri vviyttgsqa tmdernrqia eigaslikhw
```

For example, the β-lactamase α and ω fragments can be used in the present invention to complement and produce selectable activity in the bacterial periplasm in a manner that is dependent on specific interaction between the first member of putative binding pair) and the second member of the putative binding pair fused to the β-lactamase fragments. This β-lactamase based protein-protein interaction reporter system can undergo co-translational secretory translocation across the bacterial inner membrane into the periplasm, and therefore can reliably detect interactions between and among proteins.

The members of a putative binding pair which can be assayed for their binding affinity with each other, using the methods of the present invention, include any molecules capable of a binding interaction. The binding interaction between the two or more binding members may be either direct or in the form of a complex with one or more additional binding species, such as charged ions or molecules, ligands, or macromolecules. Putative binding partners, or putative binding moieties, according to the present invention, can include molecules which do not normally interact with each other, but which interact with a third molecule such that, in the presence of the third molecule, the putative binding partners are brought together. Thus, substances which influence an interaction between putative binding partners include those which stimulate a weak interaction between putative binding partners, as well as one or more molecules which mediate interaction between molecules which do not normally interact with each other. In addition, substances which influence an interaction between putative binding partners can include those which directly or indirectly affect an upstream event which results in association between the putative binding partners. For example, phosphorylation of one of the putative binding partners can endow it with the capacity to associate with another of the putative binding partners.

Exemplary putative binding pairs include membrane protein-soluble binding protein pair, a membrane protein-membrane protein binding pair, a biotin-avidin binding pair, ligand-receptor binding pair, and antibody-antigen binding pair.

In an antigen-antibody pair, for example, the antibody can be a monoclonal antibody, bispecific antibody, single-chain antibody (scAb), single-chain Fv fragment (scFv), scFv$_2$, dsFv, scFv-Fc, Fab, F(ab')$_2$, F(ab)$_3$, V$_L$, diabody, single domain antibody, camelid antibody, triabody, tetrabody, minibody, one-armed antibody, and immunoglobulin (Ig), IgM, IgE, IgA, IgD, IgG, IgG-ΔC$_H$2.

The ligand-receptor pairs of the present invention can include, for example, the following receptors Fc receptors (FcR), single-chain MHC, or single-chain T-cell receptor (scTCR). Useful ligands are, for example, monotopic membrane proteins, polytopic membrane proteins, transmembrane proteins, G protein-coupled receptors (GPCRs), ion channels, members of the SNARE protein family, integrin adhesion receptor, multi-drug efflux transporters.

Other exemplary proteins include members of the signal transduction pathway, cell surface receptors, proteins regulating apoptosis, proteins that regulate progression of the cell-cycle, proteins involved in the development of tumors, transcriptional-regulatory proteins, translation regulatory proteins, proteins that affect cell interactions, cell adhesion molecules, proteins that participate in the folding of other proteins, and proteins involved in targeting to intracellular compartments.

Members of signal transduction pathways include protein hormones and cytokines. Cytokines include those involved in signal transduction, such as interferons, chemokines, and hematopoietic growth factors. Other exemplary proteins include interleukins, lymphotoxin, transforming growth factors-a and 13, and macrophage and granulocyte colony stimulating factors. Other proteins include intracellular enzymes such as protein kinases, phosphatases and synthases.

Exemplary proteins involved in apoptosis include tumor necrosis factor (TNF), Fos ligand, interleukin-1β converting enzyme (ICE) proteases, and TNF-related apoptosis-inducing ligand (TRAIL). Proteins involved in the cell cycle include deoxyribonucleic acid (DNA) polymerases, proliferating cell nuclear antigen, telomerase, cyclins, cyclin dependent kinases, tumor suppressors and phosphatases. Proteins involved in transcription and translation include ribonucleic acid (RNA) polymerases, transcription factors, enhancer-binding proteins and ribosomal proteins. Proteins involved in cellular interactions such as cell-to-cell signaling include receptor proteins, and peptide hormones or their enhancing or inhibitory mimics.

The reporter protein fragments and one or more members of the putative binding pair are generally linked either directly or via a linker, and are generally linked by a covalent linkage. For example, when the reporter protein fragment and the members of the putative binding pair are proteins, they may be linked by methods known in the art for linking peptides.

The fragment members of reporter proteins also may include a flexible polypeptide linker separating the fragment of reporter protein from the member of the putative binding pair and allowing for their independent folding. The linker is optimally 15 amino acids or 60 Å in length (~4 Å per residue) but may be as long as 30 amino acids but preferably not more than 20 amino acids in length. It may be as short as 3 amino acids in length, but more preferably is at least 6 amino acids in length. To ensure flexibility and to avoid introducing steric hindrance that may interfere with the independent folding of the fragment domain of reporter protein and the members of the putative binding pair, the linker should be comprised of small, preferably neutral residues such as Gly, Ala, and Val, but also may include polar residues that have heteroatoms such as Ser and Met, and may also contain charged residues.

In one embodiment, the β-lactamase reporter fragments are capable of binding to one another to form an enzymatically active complex that is capable of catalyzing the conversion of a substrate to a product which is detectable, either directly or indirectly. In one embodiment, the β-lactamase reporter system can include two or more components, in a fusion protein, where the fusion proteins each comprise a putative binding protein fused to a low affinity β-lactamase reporter fragment. Thus, nucleic acids encoding the fusion proteins can be constructed, introduced into cells and expressed in cells. Alternatively, the bound β-lactamase reporter units or bound binding moieties can be detected by selecting the prokaryotic host cells expressing the fusion proteins of the present invention on a selection media which includes an antibiotic such as ampicillin.

A variety of cell-based assays can be conducted using the cells containing the fusion gene constructs. Binding of the putative binding moieties on the fusion proteins expressed in the cells can be confirmed by detecting the signal produced by the reporter fragments undergoing complementation. This signal could be, for example, a fluorescent signal which is regenerated after the reporter fragments undergo complementation.

In one embodiment of the invention, prokaryotic cells in which a the reporter fragments undergo complementation can be detected and isolated by flow cytometry or fluorescence-activated cell sorting (FACS). Methods for flow cytometry and FACS are well-known in the art (Nolan et al., "Fluorescence-activated Cell Analysis and Sorting of Viable Mammalian Cells Based on beta-D-galactosidase Activity After Transduction of *Escherichia coli* lacZ," *Proc. Natl. Acad. Sci. USA* 85:2603-2607 (1988); Webster et al., "Isolation of human myoblasts with the fluorescence-activated cell sorter," *Exp. Cell Research,* 174:252-265 (1988), which are hereby incorporated by reference in their entirety). In this way, clones of cells in which binding occurs can be isolated and propagated for further study.

Binding of the protein molecules of the present invention will depend upon factors such as pH, ionic strength, concentration of components of the assay, and temperature. In the binding assays using reporter systems described herein, the binding affinity of the first member of the putative binding pair and the second member of the putative binding pair should be strong enough to permit binding between the reporter protein fragments. In a preferred embodiment, the binding affinity of the first member of the putative binding pair and the second member of the putative binding pair should be stronger than the binding affinity of the first fragment and the second fragment of the reporter protein. When combining the first and second fusion proteins, the reconstitution of the first and second fragments into the reporter protein requires the interaction between the first and second members of the putative binding pair. Bound members of the putative binding pair are identified by expressing a functionally reconstituted reporter protein, and then the nucleotide sequences encoding for bound members of the putative binding pair are characterized by methods including electrophoresis, polymerase chain reaction (PCR), nucleotide and amino acid sequencing and the like.

In one embodiment, either one or both the first and second members of the putative binding pair can be a member of a library. The members of the putative binding pair can be parts of libraries that are constructed from cDNA, but may also be constructed from, for example, synthetic DNA, RNA and genomic DNA.

A large number of proteins synthesized in prokaryotes are translocated (transported) partially or fully to the outside of the cytoplasm by a secretory pathway. The first step of translocation involves insertion into and translocation across the cytoplasmic membrane. In gram-positive bacteria, fully translocated proteins are released into the external milieu whereas in gram negative bacteria, the proteins are translocated and released into the periplasm or are integrated into or transported across the outer membrane. The secreted proteins usually contain a secretory signal sequence (also referred to as a signal sequence or a signal peptide) that generally, but not always, contains a stretch of at least around 10 hydrophobic amino acid residues. A detailed review of the general secretory pathways (GSP) in prokaryotic bacteria is provided by Pugsley A. P., "The Complete General Secretory Pathway in Gram-negative Bacteria," *Microbiological Reviews* 57:50-108 (1993), which is hereby incorporated by reference in its entirety.

The proteins of the present invention are transported to the prokaryotic host cell's periplasm. This can be done, for example, by targeting the general secretory pathway (GSP) of the prokaryotic cells to transport the proteins across the cytoplasmic membrane. These secretory pathways (also known as translocation pathways or transport pathways) include, for example the Sec pathway, the SRP pathway and the Tat pathway.

For the purposes of the present invention, it is preferable that the proteins are maintained in an translocation competent conformation or fold. Proteins that are exported from the cytosol by the transportation pathways of prokaryotes have certain features that promote efficient translocation across membranes. These features generally, but not always, include an amino-terminal hydrophobic signal sequence that is cleaved during the translocation process. Furthermore, some feature of the protein or of the export process must ensure that the protein does not fold such that its export is prevented. This is usually done in prokaryotic cells in several different ways. The proteins may be translocated across a membrane simultaneously with translation (co-translationally) of the protein, thus ensuring that not even its secondary structures are formed in the cytoplasm. If the proteins are not co-translationally translocated then chaperones or antifolding factors may prevent folding in the cytoplasm thereby maintaining the export competent conformation (Randall et al., "SecB: A Chaperone from *Escherichia coli*," *Methods Enzymol.* 290: 444-459 (1998), which is hereby incorporated by reference in its entirety). In some cases, signal sequences act as intrapolypeptide chaperones to prevent rapid folding (Liu et al., "Physiological Role During Export for the Retardation of Folding by the Leader Peptide of Maltose-binding Protein," *Proc Natl Acad Sci USA* 86:9213-9217, which is hereby incorporated by reference in its entirety). Also the proteins that are exported post-translationally may have features in their final structures (for example, disulfide bonds) that do not form in the environment of the cytoplasm so that the proteins cannot attain their final folded conformations in the cytoplasm (Derman et al., "*Escherichia coli* Alkaline Phosphatase Fails to Acquire Disulfide Bonds When Retained in the Cytoplasm," *J. Bacteriol* 173:7719-7722, which is hereby incorporated by reference in its entirety). This is notable because antibodies are stabilized by disulfide bonds and the oxidizing environment of the bacterial periplasm is conducive for the formation of disulfide bonds.

The proteins of the present invention comprise a signal sequence (also known in the art as the targeting sequence or signal peptide) which, when expressed in a suitable host cell, directs the transport across or through the membrane. In accordance with the present invention, the fusion proteins are transported to the bacterial periplasm of gram negative bacteria. Generally, but not always, the signal peptides are located at the amino termini of fusion proteins. The signal peptide is typically cleaved following its entry into the periplasm. As noted above, at least one of the first or second fusion proteins is co-translationally transferred to periplasm of the prokaryotic host cell.

The fusion protein can have signal sequences targeting the Sec translocation pathways (Pugsley A. P., "The Complete General Secretory Pathway in Gram-negative Bacteria," Microbiological Reviews 57:50-108 (1993), Kumamoto C. A., "Molecular Chaperones and Protein Translocation across the *Escherichia coli* inner membrane," *Mol. Microbiol.* 5:19-22 (1991), which are hereby incorporated by reference in their entirety). The Sec signal sequences can be selected from the group consisting ssAppA, ssBla, ssClyA, ssLep, ssMalE, ssOmpA, ssOmpT, ssOmpX, ssPelB (*Erwinia chrysanthemi*), ssPhoA, ssRbsB, and ssYebF.

One component of the bacterial general secretory pathway that can be used in the present invention is the signal recognition pathway (SRP) (Pugsley A. P., "The Complete General Secretory Pathway in Gram-negative Bacteria," Microbiological Reviews 57:50-108 (1993), Valent Q. A., "Signal Recognition Particle Mediated Protein Targeting in *Escherichia coli*," *Antonie van Leeuwenhoek* 79:17-31 (2001), Koch et al., "Signal Recognition Particle-dependent Protein Targeting, Universal to All Kingdoms of Life," *Rev Physiol Biochem Pharmacol.* 146:55-94 (2003), which are hereby incorporated by reference in its entirety). The prokaryotic SRP is composed of one protein (Ffh) and a 4.5S RNA and is mainly involved in co-translational assembly of intergral membrane proteins (Luirink J. et al., "Mammalian and *Escherichia coli* Signal Recognition Particles," *Mol. Microbiol.* 11:9-13 (1994), which is hereby incorporated by reference in its entirety). The SRP signal sequences that can be used for the purposes of the present invention can be selected from the group consisting ssArtI, ssDsbA, ssFlgA, ssLivJ, ssSfmC, ssSTII, ssTolB, ssTorT, ssYraP and ssYraI. The major advantage of using the SRP pathways is that it can transport the protein co-translationally across the cytoplasmic membrane. This is a unique feature and ensures that the protein has little or no residence time in the cytoplasm. Using the SRP pathways also overcomes the problems and difficulties associated with translocating cytoplasmic proteins across the cytoplasmic membrane which may be due to folding of the protein into a conformation that has difficulty during translocation.

The reporter system of the present invention can include signal sequences which are related to the twin-arginine protein transport pathway (Tat pathway) (Sargent et al., "Pathfinders and Trailblazers: A Prokaryotic Targeting System for Transport of Folded Proteins," *FEMS Microbiol Lett* 254: 198-207 (2006), which is hereby incorporated by reference in its entirety). The Tat pathway for translocation is found in the membranes of many bacteria and its most remarkable feature is its ability to transport prefolded, and often oligomeric proteins across ionically sealed membranes (Berks et al., "The Tat Protein Translocation Pathway and Its Role in Microbial Physiology," *Adv Microb Physiol* 47:187-254 (2003), which is hereby incorporated by reference in its entirety). The fusion proteins of the present invention can include distinctive N-terminal signal peptides that bear a common amino acid sequence motif. This so-called "twin-arginine" motif has a consensus sequence which includes Arginine residues and are essential for efficient protein translocation using the Tat pathway. The Tat pathway has an intrinsic "quality control" activity that prevents transport of unfolded polypetides (DeLisa et al., "Folding Quality Control in the Export of Proteins by the Bacterial Twin Arginine Translocation Pathway," *Proc Natl Acad Sci USA* 100: 6115-6120 (2003) which is hereby incorporated by reference in its entirety). A major advantage of using the Tat pathways in the present invention, is its innate ability to reject immature or incorrectly assembled protein and actively select for folded substrates. The reporter system and the fusion proteins of the present invention can have signal peptides selected from the group consisting Tat signal sequences which include ssFdnG, ssFdoG, ssNapG, ssNrfC, ssHyaA, ssYnfE, ssWcaM, ssTorA, ssNapA, ssYagT, ssYcbK, ssDmsA, ssYdhX, ssYahJ, ssYedY, ssCueO, ssSufI, ssYcdB, ssTorZ, ssHybA, ssYnfF, ssHybO, ssAmiC, ssAmiA, ssYfhG, ssMdoD, ssFhuD, ssYaeI, and ssYcdO.

In one embodiment the reporter system of the present invention is such that both of the first and the second fusion proteins are transported co-translationally to the prokaryotic host cell's periplasm.

Fusion proteins of the present invention, comprise a single continuous linear polymer of amino acids which comprise the full or partial sequence of two or more distinct proteins. The construction of fusion proteins is well-known in the art. Two or more amino acids sequences may be joined chemically, for instance, through the intermediacy of a crosslinking agent. In a preferred embodiment, a fusion protein is generated by expression of a fusion gene construct in a host cell. Fusion gene constructs generally also contain replication origins active in host cells and one or more selectable markers encoding, for example, drug or antibiotic resistance. The present invention is also directed to plasmids containing expression system constructed to express fusion proteins, described supra, of the present invention. The expression systems for the fusion protein will comprise operably linked nucleic acid components in the direction of transcription nucleotide sequences encoding for (i) a promoter or other regulatory sequence functional in a prokaryotic host cell, (ii) a fragment of a reporter protein that provides for a directly selectable phenotype, (iii) a member of the putative binding pair, or a target protein or a candidate protein, (iv) an optional flexible polypeptide linker connecting the reporter protein fragment to the member of the putative binding pair and (v) a signal peptide or signal sequence. The invention is also concerned with prokaryotic host cells that contain plasmids having the sequences of the above-described expression systems.

Different fusion gene constructs encoding unique fusion proteins may be present on separate nucleic acid molecules or on the same nucleic acid molecule. Inclusion of different fusion gene constructs on the same nucleic acid molecule is advantageous, in that uptake of only a single species of nucleic acid by a host cell is sufficient to introduce sequences encoding both putative binding partners into the host cell. By contrast, when different fusion constructs are present on different nucleic acid molecules, both nucleic acid molecules must be taken up by a particular host cell for the assay to be functional. Thus, problems of cell mosaicism are avoided when both fusion gene constructs are included on the same nucleic acid molecule.

Once the fusion protein is identified, the nucleic acid construct encoding the protein is inserted into an expression system to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by Sambrook et al., Molecular Cloning: *A Laboratory Manual*, Cold Springs Laboratory Press, Cold Springs Harbor, N.Y. (1989), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

A variety of prokaryotic expression systems can be used to express the fusion proteins of the present invention. Expression vectors can be constructed which contain a promoter to direct transcription, a ribosome binding site, and a transcriptional terminator. Examples of regulatory regions suitable for this purpose in *E. coli* are the promoter and operator region of the *E. coli* tryptophan biosynthetic pathway (Yanofsky et al., "Repression is Relieved Before Attenuation in the trp Operon of *Escherichia coli* as Tryptophan Starvation Becomes Increasingly Severe,"*J. Bacteria.* 158:1018-1024 (1984), which is hereby incorporated by reference in its entirety) and the leftward promoter of phage lambda (N) (Herskowitz et al., "The Lysis-lysogeny Decision of Phage Lambda Explicit Programming and Responsiveness," *Ann. Rev. Genet.*, 14:399-445 (1980), which is incorporated by reference in its entirety). Vectors used for expressing foreign genes in bacterial hosts generally will contain a sequence for a promoter which functions in the host cell. Plasmids useful for transforming bacteria include pBR322 (Bolivar et al., "Construction and Characterization of New Cloning Vehicles II. A Multipurpose Cloning System," *Gene* 2:95-113 (1977), which is hereby incorporated by reference in its entirety), the pUC plasmids (Messing, "New M13 Vectors for Cloning," *Meth. Enzymol.* 101:20-77 (1983), Vieira et al., "New pUC-derived Cloning Vectors with Different Selectable Markers and DNA Replication Origins," *Gene* 19:259-268 (1982) which are hereby incorporated by reference in their entirety), and derivatives thereof. Plasmids may contain both viral and bacterial elements. Methods for the recovery of the proteins in biologically active form are discussed in U.S. Pat. No. 4,966,963 to Patroni and U.S. Pat. No. 4,999,422 to Galliher, which are incorporated herein by reference in their entirety. See Sambrook, et al (In *Molecular Cloning: A Laboratory Manual*, $2^{nd}$ Ed., 1989, Cold Spring Harbor Laboratory Press, Cold Spring Harbor, which is hereby incorporated by reference in its entirety) for a description of other prokaryotic expression systems and methods used for protein expression. Suitable expression vectors include those which contain replicon and control sequences that are derived from species compatible with the host cell. For example, if *E. coli* is used as a host cell, plasmids such as pUC19, pUC18 or pBR322 may be used.

Different genetic signals and processing events control many levels of gene expression (e.g., DNA transcription and messenger RNA ("mRNA") translation) and, subsequently, the amount of fusion protein that is expressed within the host cell. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression and surface display. Depending upon the host system utilized, any one of a number of suitable promoters may be used. For instance, when using *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV 5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Appropriate host cells for application of the present invention are prokaryotic host cells, such as bacterial cells. In a preferred embodiment, the host cell is a gram-negative bacteria. Host cells suitable for expressing the proteins of the present invention include any one of the more commonly available gram-negative bacteria. Suitable microorganisms include *Pseudomonas aeruginosa, Escherichia coli, Salmonella gastroenteritis (typhimirium), S. typhi, S. enteriditis, Shigella flexneri, S. sonnie, S. dysenteriae, Neisseria gonorrhoeae, N. meningitides, Haemophilus influenzae H. pleuropneumoniae, Pasteurella haemolytica, P. multilocida, Legionella pneumophila, Treponema pallidum, T. denticola, T. orales, Borrelia burgdorferi, Borrelia* spp. *Leptospira*

*interrogans, Klebsiella pneumoniae, Proteus vulgaris, P. morganii, P. mirabilis, Rickettsia prowazeki, R. typhi, R. richettsii, Porphyromonas (Bacteriodes) gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitensis, B. canis, Spirillum minus, Pseudomonas mallei, Aeromonas hydrophile, A. salmonicida*, and *Yersinia pestis*. Methods for transforming/transfecting host cells with expression vectors are well-known in the art and depend on the host system selected as described in Sambrook et al., Molecular Cloning: *A Laboratory Manual*, Cold Springs Laboratory Press, Cold Springs Harbor, N.Y. (1989), which is hereby incorporated by reference in its entirety.

As will be apparent to one of skill in the art, the present invention allows for a broad range of studies of protein-protein and other types of multi-protein interactions to be carried out quantitatively or qualitatively in prokaryotic host cells. The proteins of the present invention could be endogenous prokaryotic proteins or a heterologous/eukaryotic proteins. In what follows, non-limiting examples of different applications of the invention are provided.

Another aspect of the present invention relates to a method of identifying a candidate protein which binds a target protein. This method includes providing a first expression system comprising a nucleic acid molecule encoding a first fragment of a reporter protein molecule, a nucleic acid molecule encoding first signal sequence, and a nucleic acid molecule encoding a target protein, where the nucleic acid molecule encoding the first fragment, the nucleic acid molecule encoding the first signal sequence, and the nucleic acid molecule encoding the target protein are operatively coupled to permit their expression in a prokaryotic host cell as a first fusion protein. This method also includes providing a second expression system comprising a nucleic acid molecule encoding a second fragment of the reporter protein molecule, a nucleic acid molecule encoding a second signal sequence, and a nucleic acid molecule encoding a candidate protein, wherein the nucleic acid molecule encoding the second fragment, the nucleic acid molecule encoding the second signal sequence, and the nucleic acid molecule encoding the candidate protein are operatively coupled to permit their expression in a prokaryotic host cell as a second fusion protein. This method further includes transforming a prokaryotic host cell with the first expression system and the second expression system, culturing the transformed prokaryotic host cell under conditions effective to express the first and the second fusion proteins and to transport the first fusion protein and the second fusion protein to the prokaryotic host cell's periplasm, with at least one of the first fusion protein or the second fusion protein being co-translationally transported to the periplasm. The prokaryotic host cells with reporter protein molecule activity are detected as those where binding between the candidate protein and the target protein has occurred. The candidate protein is identified as having the ability to bind to the target protein based on whether the host cell has reporter protein activity.

The proteins that can be used as target proteins and candidate proteins are mentioned supra.

The reporter systems of the present invention can be used in many applications such as in human therapeutics, diagnostics, and prognostics, in high-throughput screening systems for the discovery and validation of pharmaceutical targets and drugs, as well as discovery of genes that modulate protein interactions. Massive parallel mapping of pair-wise protein-protein interactions within and between the proteomes of cells, tissues, and pathogenic organisms, selection of antibody fragments or other binding proteins to whole proteomes, antigen identification for antibodies, epitope identification for antibodies, high-throughput screens for inhibitors of any protein-protein interaction can be done using the methods of the present invention. In one embodiment, the reporter system can be combined with directed evolution methods and used to engineer ultra-high affinity interactions between proteins such as antibody-antigen pairs.

By combining the methods and compositions of the invention with state-of-the-art methods for construction of high-titer, high-complexity cDNA libraries, it will be possible to identify interaction partners of a specific test protein from, for example, mammalian cells (i.e., perform functional genomics at the protein level). For this application, cDNA libraries can be constructed wherein the cDNA coding sequence is fused to a sequence encoding the reporter protein fragments of the present invention. A sequence encoding a binding protein of interest will be fused to a reporter protein fragment in a first vector. In a second series of vectors, a second reporter protein fragment will be fused to a variety of different proteins that will be tested for their ability to bind to the protein of interest. Testing will be conducted by co-transformation of prokaryotic host cells with the first and one of the series of second vectors. Those test proteins which are capable of binding to the protein of interest will allow detection of a reporter signal in cells in which they are co-expressed with the protein of interest.

This aspect of the present invention, the method can be separately carried out with a plurality of second expression systems containing a plurality of different nucleic acid molecules encoding different second proteins. This plurality of different second proteins can be encoded by members of a cDNA library. The methods of the present invention, could be adapted for efficient simultaneous detection of multitudes of interactions among proteins within cells, including expressed sequence libraries, cDNA libraries, single-chain antibody fragment (scFv) libraries, and scaffolded peptide libraries. They could also be used for rapid selection of binding molecules from single-chain antibody fragment (scFv) libraries, or from scaffolded peptide libraries for use as reagents in functional genomics studies, or for identification of natural ligands and epitopes by homology. Target interactions identified using the present invention, could be used immediately to screen for candidate compounds that act as inhibitors or activators of the protein-protein interaction.

The methods disclosed herein enable the detection and quantitation of binding events in cell lysates, as well as in intact prokaryotic host cells. The detectable signal is produced by the complementing reporter fragments and can serve as an indicator of binding between the putative binding pair (or target and candidate protein), either directly or indirectly via a third substance. Signals from the complementing reporter fragments could be detected by methods which include, for example, light emission and absorbance, genetic selection such as antibiotic selection, immunological techniques, such as immunofluorescent labeling. Exemplary signals include chromogenic, fluorescent and luminescent signals. These signals can be detected and quantitated visually or through the use of spectrophotometers, fluorimeters, microscopes, scintillation counters or other instrumentation known in the art. Assay solutions can be designed and developed for a particular system. The reporter systems disclosed herein can be used to conduct assays in systems, such as buffered cell free extracts of host cells, cell interiors, solutions of cells, solutions of cell lysates, and solutions of cell fractions, such as nuclear fractions, cytoplasmic fractions, and membrane fractions. Methods for preparing assay solutions, such as enzyme assay solutions, cell extracts, and cell suspensions, known in the art may be used. For example, physiologically compatible buffers such as phosphate buffered saline may be used.

In one embodiment of this aspect of the invention, the reporter protein molecule activity can be quantitated. In a preferred embodiment, the reporter protein activity detected among various candidate proteins is compared and used to identify the strongest binding candidate protein. This comparison among the plurality of candidate proteins can also be used to determine which of a plurality of candidate proteins bind to the target protein, or to rank the candidate proteins according to their binding affinities. The reporter protein typically will have a unique enzymatic activity or structure that enables it to be distinguished from other proteins present in the prokaryotic host cell or lysate. The methods of quantification of a reporter protein activity are well known in the art. The activity of the transcribed reporter protein, or quantification of the activity of the reporter protein, provides an indirect measurement of binding between the putative members of the binding pair. Reporter assays enable the identification of binding affinity and factors that control binding between the putative members of the binding pair. Uses for reporter activity assay include, for example, identification of factors that control or influence protein-protein interactions, study of mechanisms that influence protein interactions, screening of candidate compounds or candidate genes that influence protein-protein interactions.

In reporter protein assays with poor sensitivity, it is difficult to distinguish negative results caused by the lack of expression or low-level assay sensitivity. This problem can be overcome with assays of greater sensitivity. Multiple assays are commonly used to provide controls for efficiency of transfection. In such assays, cells are transfected with a mixture of two separate plasmids, each having a reporter protein molecule controlled by different regulatory sequences. The expression of one reporter protein is controlled by different regulatory regions being studied while the other reporter gene, acting as a control, is generally constitutively expressed by a standard promoter or enhancer. The activity of the experimental reporter enzyme is normalized to the activity of the control reporter enzyme. Similarly, to understand the effects of a candidate gene or a candidate drug on protein-protein interaction, control experiments can be run in the absence of the candidate compound or gene and used to normalize data obtained in the presence of the candidate compound or gene. To provide relevant experimental information, reporter assays must be sensitive, thus enabling the detection of low levels of reporter protein in cell lines that transfect poorly. The sensitivity of a reporter gene assay is a function of the detection method as well as reporter mRNA and protein turnover, and endogenous (background) levels of the reporter activity.

Commonly used detection techniques use isotopic, calorimetric, fluorometric or luminescent enzyme substrates and immunoassay-based procedures with isotopic or color endpoints. Many of these systems, however, have disadvantages that limit their usefulness in these assays. For example, isotopic substrates and immunoassays are limited by the cost, sensitivity and inconvenience of using radioisotopes. Fluorometric systems require external light sources that must be filtered to discriminate fluorescent signal, thereby limiting the sensitivity and increasing complexity of the detection system. Furthermore, fluorescence from endogenous source can interfere with fluorometric measurements. Colorimetric systems lack the sensitivity desired for sensitive reporter gene assays. Chemiluminescent and bioluminescent assays, on the other hand, have been found to be more rapid and sensitive than colorimetric assays and fluorometric assays.

This application will also be useful in screening for agonists and antagonists of medically-relevant protein interactions. The assays and methods of the invention can also be carried out in the presence of extracellular signaling molecules, growth factors or differentiation factors, activated or inactivated genes or signals, peptides, organic compounds, drugs or synthetic analogs, or the like, whose presence or effects might alter the potential for interaction between the target protein and the candidate protein.

Another aspect of the present invention is related to a method of identifying a candidate gene which modulates the binding between a first protein and a second protein. This method includes providing a first expression system comprising a nucleic acid molecule encoding first fragment of a reporter protein molecule, a nucleic acid molecule encoding a first signal sequence, and a nucleic acid molecule encoding a first protein, where the nucleic acid molecule encoding the first fragment, the nucleic acid molecule encoding the first signal sequence, and the nucleic acid molecule encoding the first protein are operatively coupled to permit their expression in a prokaryotic host cell as a first fusion protein. This method also includes providing a second expression system for expressing the second protein comprising a nucleic acid molecule encoding a second fragment of the reporter protein molecule, a nucleic acid molecule encoding a second signal sequence, and a nucleic acid molecule encoding a second protein, where the nucleic acid molecule encoding the second fragment, the nucleic acid molecule encoding the second signal sequence, and the nucleic acid molecule encoding the second protein are operatively coupled to permit their expression in a prokaryotic host cell as a second fusion protein. This method further involves providing a candidate gene in a form suitable for expression in a prokaryotic host cell, transforming the prokaryotic host cell with the first expression system, the second expression system, and the candidate gene, and culturing the transformed prokaryotic host cell under conditions effective to, in the absence of the candidate gene, express the first fusion protein, the second fusion protein, and the protein encoded by the candidate gene and transport the first fusion protein and the second fusion protein to the prokaryotic host cell's periplasm with at least one of the first fusion protein or the second fusion protein being co-translationally transported to the periplasm. Any reporter activity in the transformed prokaryotic host cell is detected, and prokaryotic host cells, with reporter activity that is different than that achieved without transformation of the candidate gene are identified, as containing a candidate gene which modulates binding between the first and second proteins.

The proteins that can be used as the first protein and the second protein are mentioned supra.

In one embodiment of this aspect of the invention, the presence of the candidate gene decreases the reporter activity and is identified as a candidate gene whose presence inhibits the binding between the first protein and the second protein. In another embodiment the presence of the candidate gene increases the reporter activity and is identified as activating the binding between the first protein and the second protein.

In another embodiment, the method is separately carried out with a plurality of second expression systems containing a plurality of different nucleic acid molecules encoding different second proteins, such that the second proteins are encoded by members of a cDNA library. A library of all the protein members of a proteome of interest can be constructed and used. Libraries derived from nucleotide sequences that contain all members of a total protein population (i.e. a proteome) of interest may be isolated from a host cell such as a prokaryotic or a eukaryotic cell, or also from a viral host. Viral hosts that encode for oncogenes are of particular interest. Mammalian tumor cells, immune cells and endothelial cells also provide proteomes of particular interest for the present invention.

In one embodiment of this aspect of the invention, the reporter protein activity is quantitated as described supra. In a preferred embodiment, the reporter protein activity detected among various candidate genes is compared and used to identify the strongest modulator of the interaction between the first protein and the second protein. The candidate gene can modulate the protein-protein interaction in a way such that it leads to activation the interaction or it leads to the inhibition of the interaction.

Another aspect of the present invention is related to a method of identifying a candidate compound which modulates binding between a first protein and a second protein. This method includes providing a first expression system comprising a nucleic acid molecule encoding first fragment of a reporter protein molecule, a nucleic acid molecule encoding a first signal sequence, and a nucleic acid molecule encoding a first protein, where the nucleic acid molecule encoding the first fragment, the nucleic acid molecule encoding the first signal sequence, and the nucleic acid molecule encoding the first protein are operatively coupled to permit their expression in a prokaryotic host cell as a first fusion protein. This method also includes providing a second expression system for expressing the second protein comprising a nucleic acid molecule encoding a second fragment of the reporter protein molecule, a nucleic acid molecule encoding a second signal sequence, and a nucleic acid molecule encoding a second protein, where the nucleic acid encoding the second fragment, the nucleic acid encoding the second signal sequence, and the nucleic acid encoding the second protein are operatively coupled to permit their expression in a prokaryotic host cell as a second fusion protein. This method further involves providing a candidate compound, transforming a host prokaryotic cell with the first expression system and the second expression system, and culturing the transformed host prokaryotic cell under conditions effective to express the first and the second fusion proteins and transport the first fusion protein and the second fusion protein to the prokaryotic host cell's periplasm with at least one of the first fusion protein or the second fusion protein being co-translationally transported to the periplasm. The candidate compound is contacted with the cultured prokaryotic host cell. The reporter activity is detected in the transformed prokaryotic host cell, and candidate compounds contacting the prokaryotic host cells, with reporter activity that is different than that achieved in transformed prokaryotic host cells not contacted with the candidate compound are identified as modulating binding between the first protein and the second protein.

In one embodiment, the candidate compound decreases reporter activity and is identified as inhibiting binding between the first protein and the second protein. In the same manner a candidate compound, whose presence increases reporter activity is identified as activating binding between the first protein and the second protein. In another aspect of the present invention a plurality of candidate compounds could be used and screened for their effect on the protein-protein interaction.

EXAMPLES

Example 1

Construction of Vectors

All cloning was performed using standard molecular biological techniques. A gene sequence comprising a (GGGGS)$_3$-NGR linker sequence followed by residues 198-286 of TEM-1 BLA was cloned between the BamHI and HindIII sites of pDMB to create pDMB-ωBLA. Genes to be fused to the ωBLA fragment were then cloned into this vector between XbaI and SalI sites. Genes to be fused to the αBLA fragment were cloned between the KpnI and BamHI sites of vector αGS-Jun (Wehrman, T., et al., "Protein-protein Interactions Monitored in Mammalian Cells Via Complementation of Beta-lactamase Enzyme Fragments," *Proc Natl Acad Sci USA* 99:3469-3474 (2002), which is hereby incorporated by reference in its entirety). Fos and Jun leucine knockouts and scFv-GCN4 were as in (DeLisa, M. P., "Versatile Selection Technology for Intracellular Protein-protein Interactions Mediated by Bacterial Hitchhiker Transport Mechanism, "*Proc Natl Acad Sci USA* 106:3692-3697 (2009), which is hereby incorporated by reference in its entirety). Template DNA for scFvs D10, and gpd was kindly provided by Andreas Plückthun.

Example 2

Expression of Fusion Proteins and Cell Growth Assays

*E. coli* MC4100 cells were co-transformed with plasmids pDMB-P1-ωBLA (CmR) and aGS-P2 (KanR), where P1 and P2 represent proteins of interest. Cells were grown overnight at 37° C. in LB medium containing 20 µg/mL chloramphenicol (Cm) and 50 µg/mL kanamycin (Kan). Screening of cells on LB agar was performed by first normalizing overnight cultures by OD$_{600}$ and then spotting 5 µL, of serially diluted (10-10$^6$-fold) cells on LB agar plates with 12, 25, 50, or 50 µg/mL of ampicillin (Amp). In all cases, the plates were incubated 16 h at 37° C. and then imaged using a ChemiDoc System (BioRad). For MBC/MIC determination, approximately 200 colony forming units (CFUs) of each clone were plated on LB agar plates containing 0, 3, 6, 12, 25, 50, 100, 200, 400, 800, or 1600 µg/mL Amp or 20 µg/mL Cm. The minimum bacteriocidal concentration was determined as the minimum Amp concentration at which no colonies appeared on the plates. Minimum inhibitory concentration (MIC) was determined as the minimum concentration of Amp on which colony size was significantly smaller than control.

It was hypothesized that detecting protein interactions in the periplasm can be used to engineer antibody fragments with in vivo activity in the periplasm. The periplasm is ideal for antibody engineering as its oxidizing environment allows for the formation of disulfide bonds, which many antibody fragments require to function (Auf der Maur, A., et al., "Antigen-independent Selection of Stable Intracellular Single-chain Antibodies," *FEBS Lett* 508:407-12 (2001), which is hereby incorporated by reference in its entirety). The approach used in the present invention was to fuse known interacting protein domains to genes encoding two split β-lactamase fragments using a two-plasmid system (Wehrman, T., et al., "Protein-protein Interactions Monitored in Mammalian Cells Via Complementation of Beta-lactamase Enzyme Fragments," *Proc Natl Acad Sci USA* 99:3469-3474 (2002), which is hereby incorporated by reference in its entirety)(see FIG. 2A). The α fragment encodes residues 1-196 of TEM-1 Bla, while the ω fragment encodes residues 197-286 out of 286. The α fragment contains the native signal sequence of Bla (residues 1-23), which targets the C-terminally fused protein to the Sec translocon for transport into the periplasm. In the construct of the present invention, the protein of interest fused to the ω fragment is targeted to the SRP pathway for co-translational translocation.

Example 3

Antibody-Antigen Interactions are Reported in Two Cases

Figure 2A:
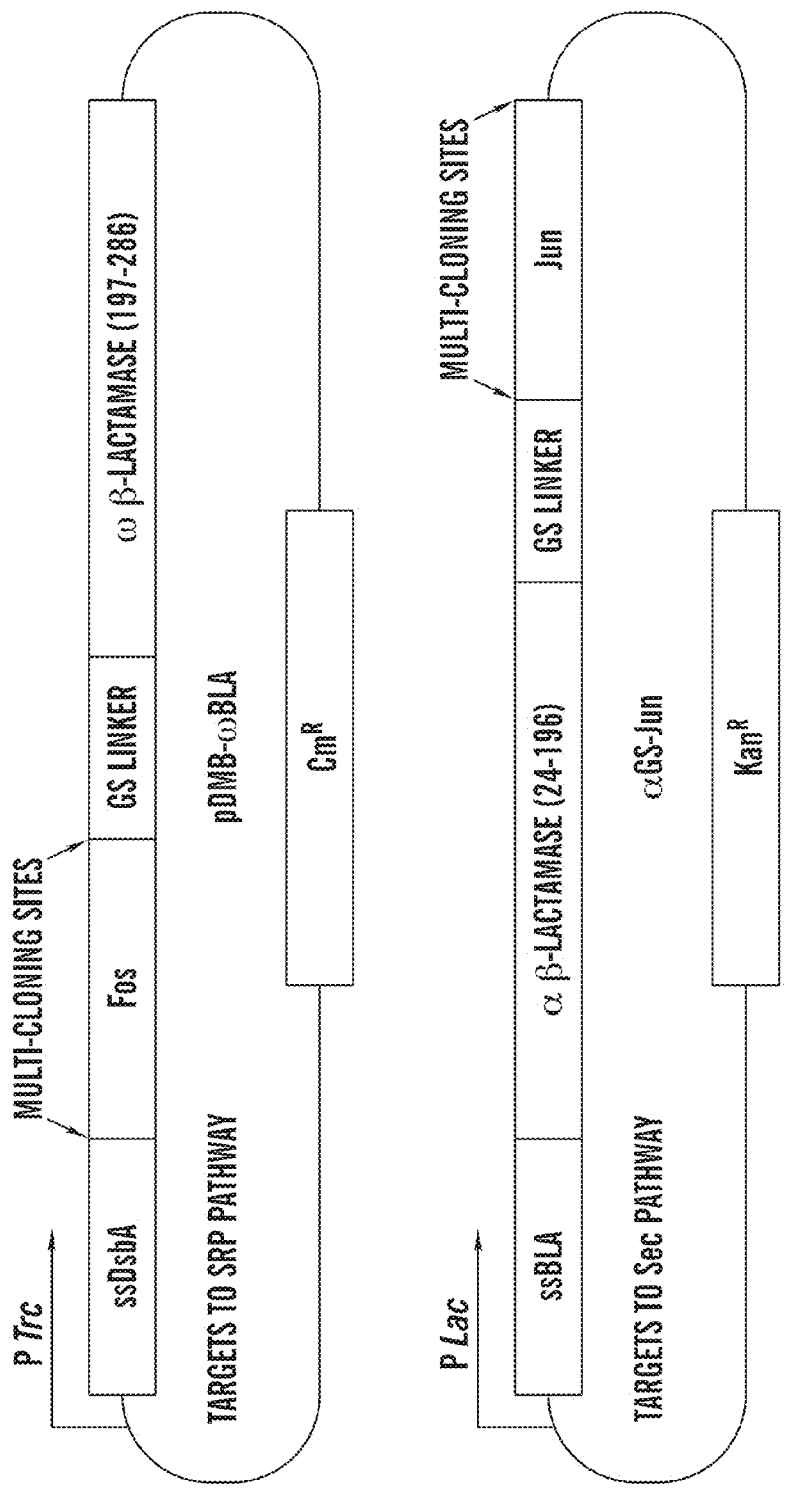
FIGS. 2A-D show the protein complementation of interacting domains.
Figure 2B:
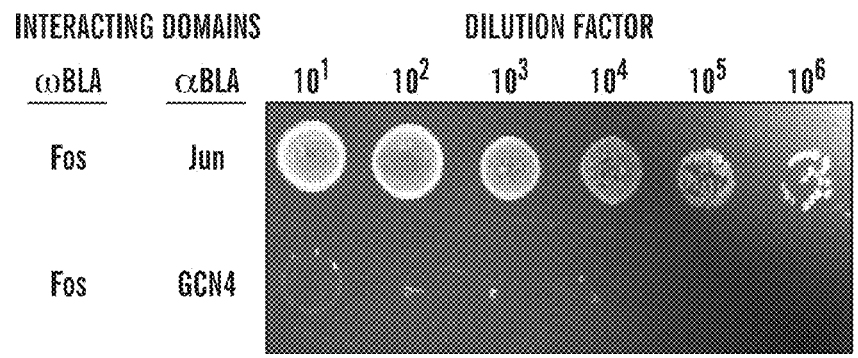
Figure 2C:
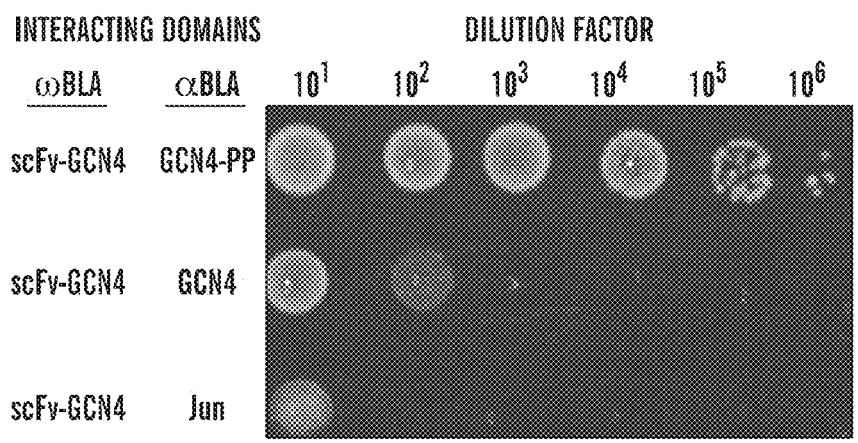
Figure 2D:
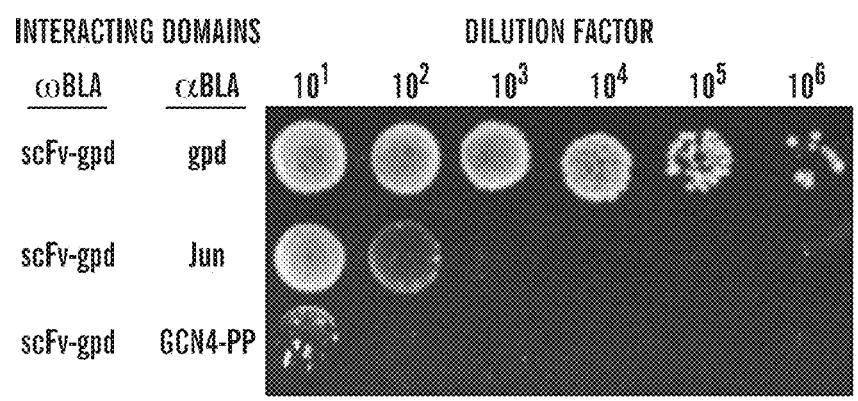

To determine the ability of the assay of the present invention to detect and eventually engineer antibody-antigen interactions, interacting protein pairs as well as non-interacting proteins were cloned into two plasmids carrying the two inactive Bla fragments (FIG. 2A). In this study, two antibody-antigen pairs were examined. First, an scFv which is known to bind the GCN4 leucine zipper was tested. In addition to the scFv and wild-type GCN4 pair, a double proline mutant, GCN4-PP as an antigen for the scFv was also tested. GCN4 is normally a homodimer, but a double proline mutant of GCN4 (GCN4-pp) exhibits reduced dimerization, thereby reducing the amount of inactive α/α dimers in the assay. FIGS. 2B-D show the results of spot plating of the interacting pairs, with α-Jun as a negative control. The spot plates correspond to a 16-fold higher MBC (minimum bacteriocidal concentration, see Example 2 for full definition of MIC/MBC) on ampicillin for GCN4-PP and a 2-fold higher MBC for the GCN4 wild-type (homodimer). A difference of this magnitude is promising for future library selection processes.

In the case of GCN4, an antibody fragment that binds a leucine zipper, a short peptide fragment was already tested. Since a goal of this assay is engineering protein-protein interactions, an antibody fragment with a protein antigen was tested. D10, an scFv with affinity for the phage protein gpD, an 11.4 kDa capsid protein from bacteriophage lambda was used (Koch, H., et al., "Direct Selection of Antibodies from Complex Libraries with the Protein Fragment Complementation Assay," *J Mol Biol* 357:427-441 (2006), which is hereby incorporated by reference in its entirety). Indeed, the results with D10 were similar (spot plating shown in FIGS. 2B-D), with an MBC roughly 8-fold higher than the Jun negative control and 16-fold higher than the GCN4-PP negative control.

Example 4

Leucine Zipper Interactions are Reported Reliably

Figure 3A:
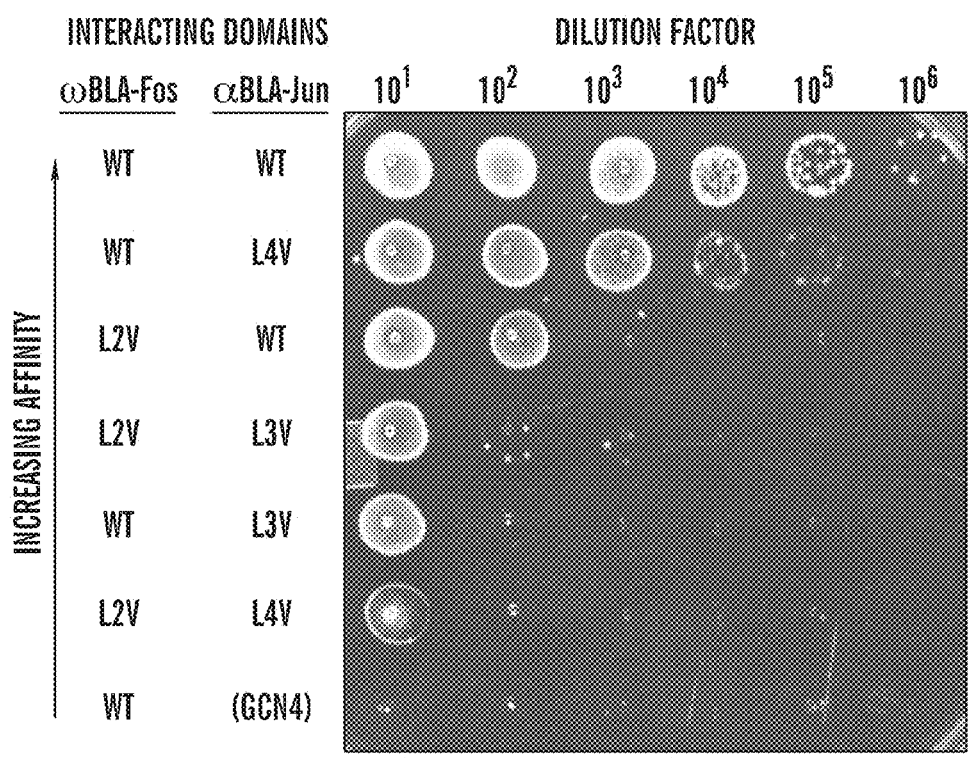
FIGS. 3A-B show the interaction of Fos and Jun variants.
Figure 3B:
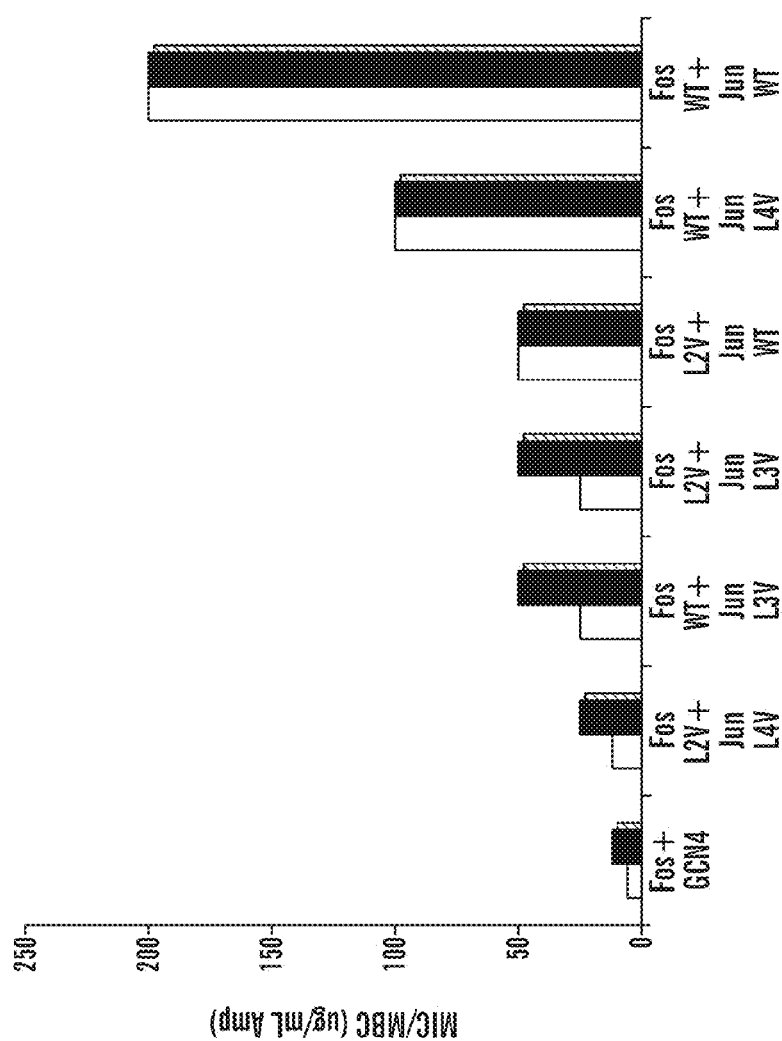

The hydrophobic interaction between Fos and Jun leucine zippers is well documented and these proteins are often used as standards for protein interaction (Wehrman, T., et al., "Protein-protein Interactions Monitored in Mammalian Cells via Complementation of Beta-lactamase Enzyme Fragments," *Proc Natl Acad Sci USA* 99:3469-3474 (2002), which is hereby incorporated by reference in its entirety). The $K_D$ of their interaction has been reported in the nanomolar range (Pernelle, C., et al., "An Efficient Screening Assay for the Rapid and Precise Determination of Affinities between Leucine Zipper Domains," *Biochemistry* 32:11682-11687 (1993), which is hereby incorporated by reference in its entirety). In the present study, Fos was fused to the ω fragment and Jun to the α fragment of β-lactamase (Bla). As a negative control, a potential binding partner of the leucine zipper GCN4 was incorporated, which does not bind Fos. When placed in the PCA, Fos and Jun were found to have ampicillin activity well above that of the negative control (FIG. 2C). After successful spot plating, the interactions were further characterized by constructing a series of point mutants that have been shown to have lower affinity (due to knockout of leucine residues). The MIC/MBC of these interactions and spot plating of these mutants can be found in FIG. 3. It is notable that the assay is apparently able to correlate Bla activity with levels of interaction along a spectrum of affinities.

It is shown that antibody-antigen reactions show a large difference in MIC/MBC from non-specific interactions. This can be used to select interacting pairs from a library of antibody fragments. The Tomlinson libraries, libraries of scFv antibody fragments with randomized complementarity determining regions, provide huge diversity. Normally, these libraries are used to isolate binding by phage display. The present invention is also related to cloning such libraries into the reporter system of the present invention, genetically fusing the scFvs to the ω fragment of Bla and selecting for interactions with a desirable antigen. In order to provide a well-folded, soluble antigen, the *E. coli* maltose binding protein can be used as a potential binding substrate. After cloning the library, 2 plasmids can be co-transformed: (1) scFv library-ω-Bla and (2) α-Bla-MalE, then selected for growth on ampicillin plates. The resulting hits can be analyzed by surface plasmon resonance (BIACore) to determine dissociation constants and further evolved via the creation of error-prone PCR libraries (with a target error rate of 3-4 mutations per gene) and selection on increasing ampicillin concentration media. Such a study will serve two purposes: (1) the selection of a novel antibody-antigen interaction and (2) the study of enrichment of affinity and its effect on Bla activity. The present invention has demonstrated that Bla activity can change with affinity and increasing affinity will provide a chance not only to track the correlation of ampicillin activity with affinity, but also the upper and lower bounds of affinity capable of detection in this assay. An additional use for this assay is selection for interactions of protein antigens with full-length IgGs, produced in the periplasm fused to a Bla fragment, then selected in the manner above.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A reporter system for detection of protein-protein interactions in the periplasm of a prokaryotic host cell, said system comprising:
a first expression system comprising:
a nucleic acid molecule encoding a first fragment of a reporter protein molecule;
a nucleic acid molecule encoding a first signal sequence directed to a signal recognition particle (SRP) transport pathway; and
a nucleic acid molecule encoding a first member of a putative binding pair, wherein said nucleic acid molecule encoding the first fragment, said nucleic acid molecule encoding the first signal sequence, and said nucleic acid molecule encoding the first member of the putative binding pair are operatively coupled to permit their expression in a prokaryotic host cell as a first fusion protein and a second expression system comprising:
a nucleic acid molecule encoding a second fragment of the reporter protein molecule;
a nucleic acid molecule encoding a second signal sequence; and
a nucleic acid molecule encoding a second member of the putative binding pair, wherein said nucleic acid molecule encoding the second fragment, said nucleic acid molecule encoding the second signal sequence, and said nucleic acid molecule encoding the second member of the putative binding pair are operatively coupled to permit their expression in a prokaryotic host cell as a second fusion protein, wherein the first signal sequence and optionally the second signal sequence are capable of directing co-translational transport of at least one of the fusion proteins, when expressed in a prokaryotic host cell, into the host cell periplasm where, when present, the first and second members of the putative binding pair bind together and the first and second fragments of the reporter protein molecule are reconstituted, thereby producing an active reporter protein.

2. The reporter system according to claim 1, wherein both the first signal sequence and the second signal sequence are capable of directing co-translational transport of the first and the second fusion proteins to the periplasm.

3. The reporter system according to claim 1, wherein the first member of the putative binding pair and the second member of the putative binding pair have a binding affinity which is stronger than the binding affinity of the first fragment and the second of the reporter protein.

4. The reporter system according to claim 1, wherein said reporter protein molecule is selected from the group consisting of a monomeric protein, a multimeric protein, a monomeric receptor, a multimeric receptor, a multimeric biomolecular complex, adenylate cyclase, alkaline phosphatase, β-lactamase, cellulase, chloramphenicol acetyl transferase (CAT), disulfide bond oxidase A (DsbA), maltose binding protein (MBP), methyltransferase, dihydrofolate reductase (DHFR), luciferase, thymidylate synthase, thymidine kinase, Trp1 N-(5'-phosphoribosyl)-anthranilate isomerase, ubiquitin, and fluorescent proteins.

5. The reporter system according to claim 4, wherein the reporter protein molecule is β-lactamase.

6. The reporter protein molecule according to claim 5, wherein the first fragment and the second fragment of the reporter protein molecule, respectively, comprise β-lactamase's α fragment having the amino acid sequence of SEQ ID NO: 2, and β lactamase's ω fragment having the amino acid sequence of SEQ ID NO: 3.

7. The reporter system according to claim 1, wherein the second signal sequence is directed to a transport pathway selected from the group consisting of Sec pathway, SRP pathway, and Tat pathway.

8. The reporter system according to claim 7, wherein the first signal sequence and the second signal sequences are directed to the SRP pathway and are selected from the group consisting ssArtI, ssDsbA, ssFlgA, ssLivJ, ssSfmC, ssSTII, ssTolB, ssTorT, ssYraP, and ssYraI.

9. The reporter system according to claim 7, wherein the second signal sequence is directed to the Sec pathway and is selected from the group consisting ssAppA, ssBla, ssClyA, ssLep, ssMalE, ssOmpA, ssOmpT, ssOmpX, ssPelB (*Erwinia chrysanthemi*), ssPhoA, ssRbsB, and ssYebF.

10. The reporter system according to claim 7, wherein the second signal sequence is directed to the Tat pathway and is selected from the group consisting ssFdnG, ssFdoG, ssNapG, ssNrfC, ssHyaA, ssYnfE, ssWcaM, ssTorA, ssNapA, ssYagT, ssYcbK, ssDmsA, ssYdhX, ssYahJ, ssYedY, ssCueO, ssSufI, ssYcdB, ssTorZ, ssHybA, ssYnfF, ssHybO, ssAmiC, ssAmiA, ssYfhG, ssMdoD, ssFhuD, ssYaeI, and ssYcdO.

11. The reporter system according to claim 1, wherein the prokaryotic host cell is a gram negative bacteria.

12. The reporter system according to claim 1, wherein the putative binding pair is selected from the group of proteins consisting a membrane protein-soluble binding protein pair, a membrane protein-membrane protein binding pair, a biotin-avidin binding pair, ligand-receptor binding pair, and an antibody-antigen pair.

13. The reporter system according to claim 12, wherein the putative binding pair is an antibody-antigen pair, wherein the antibody is selected from the group consisting of monoclonal antibody, bispecific antibody, single-chain antibody (scAb), single-chain Fv fragment (scFv), scFv$_2$, dsFv, scFv-Fc, Fab, F(ab')$_2$, F(ab')$_3$, V$_L$, diabody, single domain antibody, camelid antibody, triabody, tetrabody, minibody, one-armed antibody, and immunoglobulin (Ig), IgM, IgE, IgA, IgD, IgG, IgG-ΔC$_H$2, and wherein the antigen is selected from the group consisting of cell surface receptors, proteins regulating apoptosis, proteins that regulate progression of the cell-cycle, proteins involved in the development of tumors, transcriptional-regulatory proteins, translation regulatory proteins, proteins that affect cell interactions, cell adhesion molecules, proteins which are members of ligand-receptor pairs, proteins that participate in the folding of other proteins, SNARE protein family, and proteins involved in targeting to intracellular compartments.

14. The reporter system according to claim 12, wherein the putative binding pair is a receptor-ligand pair, wherein the receptor is selected from the group consisting of Fc receptors (FcR), single-chain MHC, and single-chain T-cell receptor (sc-TCR).

15. The reporter system according to claim 12, wherein the putative binding pair is a membrane protein-membrane protein binding pair or membrane protein-soluble protein binding pair, wherein the membrane protein is selected from the group consisting of monotopic membrane proteins, polytopic membrane proteins, transmembrane proteins, G protein-coupled receptors (GPCRs), ion channels, SNARE protein family, integrin adhesion receptor, and multi-drug efflux transporters.

16. A method of identifying a candidate protein which binds a target protein, said method comprising:
   a) providing a first expression system comprising:
      a nucleic acid molecule encoding a first fragment of a reporter protein molecule;
      a nucleic acid molecule encoding first signal sequence directed to a signal recognition particle (SRP) transport pathway; and
      a nucleic acid molecule encoding a target protein, wherein said nucleic acid molecule encoding the first fragment, said nucleic acid molecule encoding the first signal sequence, and said nucleic acid molecule encoding the target protein are operatively coupled to permit their expression in a prokaryotic host cell as a first fusion protein and
   b) providing a second expression system comprising:
      a nucleic acid molecule encoding a second fragment of the reporter protein molecule;
      a nucleic acid molecule encoding a second signal sequence; and
      a nucleic acid molecule encoding a candidate protein, wherein said nucleic acid molecule encoding the second fragment, said nucleic acid molecule encoding the second signal sequence, and said nucleic acid molecule encoding the candidate protein are operatively coupled to permit their expression in a prokaryotic host cell as a second fusion protein;
   c) transforming a prokaryotic host cell with said first expression system and said second expression system;
   d) culturing the transformed prokaryotic host cell under conditions effective to express the first and the second fusion proteins and to transport the first fusion protein and the second fusion protein to the prokaryotic host cell's periplasm, wherein the first signal sequence and optionally the second signal sequence are capable of directing co-translational transport of at least one of the fusion proteins, when expressed in a prokaryotic host cell, into the host cell periplasm;
   e) detecting the prokaryotic host cells with reporter protein molecule activity as those where binding between the candidate protein and the target protein has occurred; and
   f) identifying the candidate protein as having the ability to bind to the target protein based on whether the host cell has reporter protein activity.

17. The method according to claim 16, wherein the target and candidate proteins are selected from the group of proteins consisting of a membrane protein-soluble binding protein pair, a membrane protein-membrane protein binding pair, a biotin-avidin binding pair, ligand-receptor binding pair, and an antibody-antigen pair.

18. The method according to claim 16, wherein said reporter protein molecule is selected from the group consisting of a monomeric protein, a multimeric protein, a monomeric receptor, a multimeric receptor, a multimeric biomolecular complex, adenylate cyclase, alkaline phosphatase, β-lactamase, cellulase, chloramphenicol acetyl transferase (CAT), disulfide bond oxidase A (DsbA), maltose binding protein (MBP), methyltransferase, dihydrofolate reductase (DHFR), luciferase, thymidylate synthase, thymidine kinase, Trp1 N-(5'-phosphoribosyl)-anthranilate isomerase, ubiquitin, and fluorescent proteins.

19. The method according to claim 16, wherein the second signal sequence is directed to a transport pathway selected from the group consisting of Sec pathway, SRP pathway, and Tat pathway.

20. The method according to claim 16, wherein the prokaryotic host cell is a gram negative bacteria.

21. The method according to claim 16 wherein said detecting is carried out quantitatively.

22. The method according to claim 21 further comprising:
comparing the quantitative reporter protein activity detected among various candidate proteins to identify the strongest binding candidate protein.

23. The method according to claim 16, wherein said method is carried out to determine which of a plurality of candidate proteins bind to the target protein.

24. A method of identifying a candidate gene which modulates binding between a first protein and a second protein, said method comprising:
a) providing a first expression system comprising
a nucleic acid molecule encoding first fragment of a reporter protein molecule;
a nucleic acid molecule encoding a first signal sequence directed to a signal recognition particle (SRP) transport pathway; and
a nucleic acid molecule encoding a first protein, wherein said nucleic acid molecule encoding the first fragment, said nucleic acid molecule encoding the first signal sequence, and said nucleic acid molecule encoding the first protein are operatively coupled to permit their expression in a prokaryotic host cell as a first fusion protein;
b) providing a second expression system for expressing the second protein comprising:
a nucleic acid molecule encoding a second fragment of the reporter protein molecule;
a nucleic acid molecule encoding a second signal sequence; and
a nucleic acid molecule encoding a second protein, wherein said nucleic acid molecule encoding the second fragment, said nucleic acid molecule encoding the second signal sequence, and said nucleic acid molecule encoding the second protein are operatively coupled to permit their expression in a prokaryotic host cell as a second fusion protein;
c) providing a candidate gene in a form suitable for expression in a prokaryotic host cell;
d) transforming the prokaryotic host cell with the first expression system, the second expression system, and the candidate gene;
e) culturing the transformed prokaryotic host cell under conditions effective to, in the absence of the candidate gene, express the first fusion protein, the second fusion protein, and the protein encoded by the candidate gene and transport the first fusion protein and the second fusion protein to the prokaryotic host cell's periplasm, wherein the first signal sequence and optionally the second signal sequence are capable of directing co-translational transport of at least one of the fusion proteins, when expressed in a prokaryotic host cell, into the host cell periplasm;
f) detecting any reporter activity in the transformed prokaryotic host cell; and
g) identifying prokaryotic host cells, with reporter activity that is different than that achieved without transformation of the candidate gene, as containing a candidate gene which modulates binding between the first and second proteins.

25. The method according to claim 24, wherein a candidate gene, whose presence decreases reporter activity is identified as inhibiting binding between the first protein and the second protein.

26. The method according to claim 24, wherein a candidate gene, whose presence increases reporter activity is identified as activating binding between the first protein and the second protein.

27. The method according to claim 24, wherein said method is separately carried out with a plurality of second expression systems containing a plurality of different nucleic acid molecules encoding different second proteins, wherein the second proteins are encoded by members of a cDNA library.

28. The method according to claim 24, wherein the first protein and the second protein have a binding affinity which is stronger than the binding affinity of the first fragment and the second fragment of the reporter protein.

29. The method according to claim 24, wherein said reporter protein molecule is selected from the group consisting of a monomeric protein, a multimeric protein, a monomeric receptor, a multimeric receptor, a multimeric biomolecular complex, adenylate cyclase, alkaline phosphatase, β-lactamase, cellulase, chloramphenicol acetyl transferase (CAT), disulfide bond oxidase A (DsbA), maltose binding protein (MBP), methyltransferase, dihydrofolate reductase (DHFR), luciferase, thymidylate synthase, thymidine kinase, Trp1 N-(5'-phosphoribosyl)-anthranilate isomerase, ubiquitin, and fluorescent proteins.

30. The method according to claim 24, wherein the second signal sequence is directed to a transport pathway selected from the group consisting of Sec pathway, SRP pathway, and Tat pathway.

31. The method according to claim 24, wherein the prokaryotic host cell is a gram negative bacteria.

32. The method according to claim 24, wherein the first and the second protein are selected from the group of proteins consisting of a membrane protein-soluble binding protein pair, a membrane protein-membrane protein binding pair, a biotin-avidin binding pair, ligand-receptor binding pair, and an antibody-antigen pair.

33. The method according to claim 24, wherein said detecting is carried out quantitatively.

34. The method according to claim 33 further comprising:
comparing the quantitative reporter protein activity detected among various candidate genes to identify the candidate gene which is the strongest modulator of the interaction between the first protein and the second protein.

35. A method of identifying a candidate compound which modulates binding between a first protein and a second protein, said method comprising:
a) providing a first expression system comprising
a nucleic acid molecule encoding first fragment of a reporter protein molecule;

a nucleic acid molecule encoding a first signal sequence directed to a signal recognition particle (SRP) transport pathway; and a nucleic acid molecule encoding a first protein, wherein said nucleic acid molecule encoding the first fragment, said nucleic acid molecule encoding the first signal sequence, and said nucleic acid molecule encoding the first protein are operatively coupled to permit their expression in a prokaryotic host cell as a first fusion protein b) providing a second expression system for expressing the second protein comprising:

a nucleic acid molecule encoding a second fragment of the reporter protein molecule;

a nucleic acid molecule encoding a second signal sequence; and a nucleic acid molecule encoding a second protein, wherein said nucleic acid encoding the second fragment, said nucleic acid encoding the second signal sequence, and said nucleic acid encoding the second protein are operatively coupled to permit their expression in a prokaryotic host cell as a second fusion protein;

c) providing a candidate compound;

d) transforming a host prokaryotic cell with the first expression system and the second expression system;

e) culturing the transformed host prokaryotic cell under conditions effective to express the first and the second fusion proteins and transport the first fusion protein and the second fusion protein to the prokaryotic host cell's periplasm, wherein the first signal sequence and optionally the second signal sequence are capable of directing co-translational transport of at least one of the fusion proteins, when expressed in a prokaryotic host cell, into the host cell periplasm;

f) contacting the candidate compound with the cultured prokaryotic host cell;

g) detecting reporter activity in the transformed prokaryotic host cell; and h) identifying candidate compounds contacting the prokaryotic host cells, with reporter activity that is different than that achieved in transformed prokaryotic host cells not contacted with the candidate compound, as modulating binding between the first protein and the second protein.

36. The method according to claim 35, wherein the candidate compound, whose presence decreases reporter activity is identified as inhibiting binding between the first protein and the second protein.

37. The method according to claim 35, wherein a candidate compound, whose presence increases reporter activity is identified as activating binding between the first protein and the second protein.

38. The method according to claim 35, wherein the binding affinity of the first protein and the second protein is stronger than the binding affinity of the first and second fragments of the reporter protein.

39. The method according to claim 35, wherein said reporter protein molecule is selected from a group consisting of a monomeric protein, a multimeric protein, a monomeric receptor, a multimeric receptor, a multimeric biomolecular complex, adenylate cyclase, alkaline phosphatase, β-lactamase, cellulase, chloramphenicol acetyl transferase (CAT), disulfide bond oxidase A (DsbA), maltose binding protein (MBP), methyltransferase, dihydrofolate reductase (DHFR), luciferase, thymidylate synthase, thymidine kinase, Trp1 N-(5'-phosphoribosyl)-anthranilate isomerase, ubiquitin, and fluorescent proteins.

40. The method according to claim 37, wherein the second signal sequence is directed to a transport pathway selected from the group consisting of Sec pathway, SRP pathway, and the Tat pathway.

41. The method according to claim 35, wherein the first and the second protein are selected from the group of proteins consisting of a membrane protein-soluble binding protein pair, a membrane protein-membrane protein binding pair, a biotin-avidin binding pair, ligand-receptor binding pair, and an antibody-antigen pair.

42. The method according to claim 35, wherein the prokaryotic host cell is a gram negative bacteria.

43. The method according to claim 35, wherein said detecting is carried out quantitatively.

44. The method according to claim 35 further comprising: comparing the quantitative reporter protein activity detected among various candidate compounds to identify the compound which is the strongest modulator of the interaction between the first protein and the second protein.

45. The method according to claim 35, wherein the said method is carried out with a plurality of candidate compounds.

46. A reporter system for detection of protein-protein interactions in the periplasm of a prokaryotic host cell, said system comprising:

a first expression system comprising:

a nucleic acid molecule encoding an alpha (α) fragment of a β-lactamase reporter protein molecule;

a nucleic acid molecule encoding a first signal sequence directed to a signal recognition particle (SRP) transport pathway; and a nucleic acid molecule encoding a first member of a putative binding pair, wherein said nucleic acid molecule encoding the alpha (α) fragment, said nucleic acid molecule encoding the first signal sequence, and said nucleic acid molecule encoding the first member of the putative binding pair are operatively coupled to permit their expression in a prokaryotic host cell as a first fusion protein and a second expression system comprising:

a nucleic acid molecule encoding an omega (ω) fragment of the β-lactamase reporter protein molecule;

a nucleic acid molecule encoding a second signal sequence; and a nucleic acid molecule encoding a second member of the putative binding pair, wherein said nucleic acid molecule encoding the omega (ω) fragment, said nucleic acid molecule encoding the second signal sequence, and said nucleic acid molecule encoding the second member of the putative binding pair are operatively coupled to permit their expression in a prokaryotic host cell as a second fusion protein, wherein the first signal sequence and optionally the second signal sequence are capable of directing co-translational transport of at least one of the fusion proteins, when expressed in a prokaryotic host cell, into the host cell periplasm where, when present, the first and second members of the putative binding pair bind together and alpha (α) and omega (ω) fragments of the β-lactamase reporter protein molecule are reconstituted, thereby producing an active reporter β-lactamase protein, wherein the bacterial host cell is a gram negative bacteria.

47. The reporter system according to claim 46, wherein both the first signal sequence and the second signal sequence are capable of directing co-translational transport of the first and the second fusion proteins to the periplasm.

48. The reporter system according to claim 46, wherein the first member of the putative binding pair and the second member of the putative binding pair have a binding affinity which is stronger than the binding affinity of the alpha ($\alpha$) fragment and the omega ($\omega$) fragment of the reporter protein.

49. The reporter system according to claim 46, wherein the second signal sequence is directed to a transport pathway selected from the group consisting of Sec pathway, SRP pathway, and Tat pathway.

50. The reporter system according to claim 49, wherein the first signal sequence and the second signal sequences are directed to the SRP pathway and are selected from the group consisting ssArtI, ssDsbA, ssFlgA, ssLivJ, ssSfmC, ssSTII, ssTolB, ssTorT, ssYraP, and ssYraI.

51. The reporter system according to claim 49, wherein the second signal sequence is directed to the Sec pathway and is selected from the group consisting ssAppA, ssBla, ssClyA, ssLep, ssMalE, ssOmpA, ssOmpT, ssOmpX, ssPelB (*Erwinia chrysanthemi*), ssPhoA, ssRbsB, and ssYebF.

52. The reporter system according to claim 49, wherein the second signal sequence is directed to the Tat pathway and is selected from the group consisting ssFdnG, ssFdoG, ssNapG, ssNrfC, ssHyaA, ssYnfE, ssWcaM, ssTorA, ssNapA, ssYagT, ssYcbK, ssDmsA, ssYdhX, ssYahJ, ssYedY, ssCueO, ssSufI, ssYcdB, ssTorZ, ssHybA, ssYnfF, ssHybO, ssAmiC, ssAmiA, ssYfhG, ssMdoD, ssFhuD, ssYaeI, and ssYcdO.

53. The reporter system according to claim 46, wherein the putative binding pair is selected from the group of proteins consisting a membrane protein-soluble binding protein pair, a membrane protein-membrane protein binding pair, a biotin-avidin binding pair, ligand-receptor binding pair, and an antibody-antigen pair.

54. The reporter system according to claim 53, wherein the putative binding pair is an antibody-antigen pair, wherein the antibody is selected from the group consisting of monoclonal antibody, bispecific antibody, single-chain antibody (scAb), single-chain Fv fragment (scFv), scFv$_2$, dsFv, scFv-Fc, Fab, F(ab')$_2$, F(ab')$_3$, V$_L$, diabody, single domain antibody, camelid antibody, triabody, tetrabody, minibody, one-armed antibody, and immunoglobulin (Ig), IgM, IgE, IgA, IgD, IgG, IgG-$\Delta C_H 2$, and wherein the antigen is selected from the group consisting of cell surface receptors, proteins regulating apoptosis, proteins that regulate progression of the cell-cycle, proteins involved in the development of tumors, transcriptional-regulatory proteins, translation regulatory proteins, proteins that affect cell interactions, cell adhesion molecules, proteins which are members of ligand-receptor pairs, proteins that participate in the folding of other proteins, SNARE protein family, and proteins involved in targeting to intracellular compartments.

55. The reporter system according to claim 53, wherein the putative binding pair is a receptor-ligand pair, wherein the receptor is selected from the group consisting of Fc receptors (FcR), single-chain MHC, and single-chain T-cell receptor (sc-TCR).

56. The reporter system according to claim 53, wherein the putative binding pair is a membrane protein-membrane protein binding pair or membrane protein-soluble protein binding pair, wherein the membrane protein is selected from the group consisting of monotopic membrane proteins, polytopic membrane proteins, transmembrane proteins, G protein-coupled receptors (GPCRs), ion channels, SNARE protein family, integrin adhesion receptor, and multi-drug efflux transporters.

* * * * *

SEQUENCE LISTING

<160> NUMBER OF SEQ ID NOS: 3

<210> SEQ ID NO 1
<211> LENGTH: 286
<212> TYPE: PRT
<213> ORGANISM: Escherichia coli

<400> SEQUENCE: 1

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Thr Thr Ile Gly Gly Pro Lys
        130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 2
<211> LENGTH: 196
<212> TYPE: PRT
<213> ORGANISM: Escherichia coli

<400> SEQUENCE: 2

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80
```

```
Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
            115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
                180                 185                 190

Thr Gly Glu Leu
        195

<210> SEQ ID NO 3
<211> LENGTH: 90
<212> TYPE: PRT
<213> ORGANISM: Escherichia coli

<400> SEQUENCE: 3

Leu Thr Leu Ala Ser Arg Gln Gln Leu Ile Asp Trp Met Glu Ala Asp
1               5                   10                  15

Lys Val Ala Gly Pro Leu Leu Arg Ser Ala Leu Pro Ala Gly Trp Phe
            20                  25                  30

Ile Ala Asp Lys Ser Gly Ala Gly Glu Arg Gly Ser Arg Gly Ile Ile
            35                  40                  45

Ala Ala Leu Gly Pro Asp Gly Lys Pro Ser Arg Ile Val Val Ile Tyr
        50                  55                  60

Thr Thr Gly Ser Gln Ala Thr Met Asp Glu Arg Asn Arg Gln Ile Ala
65                  70                  75                  80

Glu Ile Gly Ala Ser Leu Ile Lys His Trp
                85                  90
```